(12) United States Patent
Boughner et al.

(10) Patent No.: US 12,150,817 B2
(45) Date of Patent: Nov. 26, 2024

(54) MEDICAL DEVICE ANCHORING APPARATUS AND PLACEMENT TOOL

(71) Applicant: Medtronic, Inc., Minneapolis, MN (US)

(72) Inventors: Kyle J. Boughner, Ramsey, MN (US); Carmen Dimovski, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 701 days.

(21) Appl. No.: 17/101,723

(22) Filed: Nov. 23, 2020

(65) Prior Publication Data

US 2021/0177538 A1    Jun. 17, 2021

Related U.S. Application Data

(60) Provisional application No. 62/947,917, filed on Dec. 13, 2019.

(51) Int. Cl.
*A61B 90/10* (2016.01)
*A61B 17/32* (2006.01)
*A61M 25/06* (2006.01)
*A61N 1/372* (2006.01)

(52) U.S. Cl.
CPC .. *A61B 90/10* (2016.02); *A61B 2017/320052* (2013.01); *A61B 2090/103* (2016.02); *A61M 25/06* (2013.01); *A61N 1/372* (2013.01)

(58) Field of Classification Search
CPC ... A61B 90/10; A61B 90/11; A61B 2090/103; A61B 2017/320052; A61B 25/06; A61B 34/20; A61N 1/0529; A61N 1/0534; A61N 1/0539; A61N 1/372; A61F 2/2875
See application file for complete search history.

(56) References Cited

U.S. PATENT DOCUMENTS

2002/0052610 A1* 5/2002 Skakoon ............. A61N 1/0539
606/129
2002/0156372 A1 10/2002 Skakoon et al.
(Continued)

FOREIGN PATENT DOCUMENTS

WO    2009/055746    4/2009

OTHER PUBLICATIONS

U.S. Appl. No. 62/400,140.
(Continued)

*Primary Examiner* — Robert A Lynch
(74) *Attorney, Agent, or Firm* — Mueting Raasch Group

(57) ABSTRACT

Various embodiments of a placement tool for an apparatus to be fastened to a cranium with a fastener around a burr hole formed through the cranium are disclosed. The placement tool includes a receptacle adapted to hold the fastener, where the receptacle includes a channel extending between an upper opening of the receptacle and a lower opening of the receptacle along a channel axis. The placement tool further includes a retainer disposed within the channel of the receptacle, where the retainer includes a recess or a protrusion adapted to restrain the fastener against movement. The fastener opening of the apparatus is configured to align with the channel axis of the channel of the receptacle when the placement tool is engaged with the apparatus.

25 Claims, 15 Drawing Sheets

(56) References Cited

U.S. PATENT DOCUMENTS

2009/0112327 A1* 4/2009 Lane .................. A61B 90/10
                                              623/16.11
2013/0066410 A1* 3/2013 Funderburk ......... A61N 1/0539
                                              607/116
2019/0060637 A1   2/2019 Duijsens et al.

OTHER PUBLICATIONS

U.S. Appl. No. 62/446,923.
Extended European Search Report from EP Application No. 20212507.6 dated May 10, 2021, 10 pages.
Extended European Search Report from EP Application No. 20213507.6 dated May 10, 2021, 10 pages.

* cited by examiner

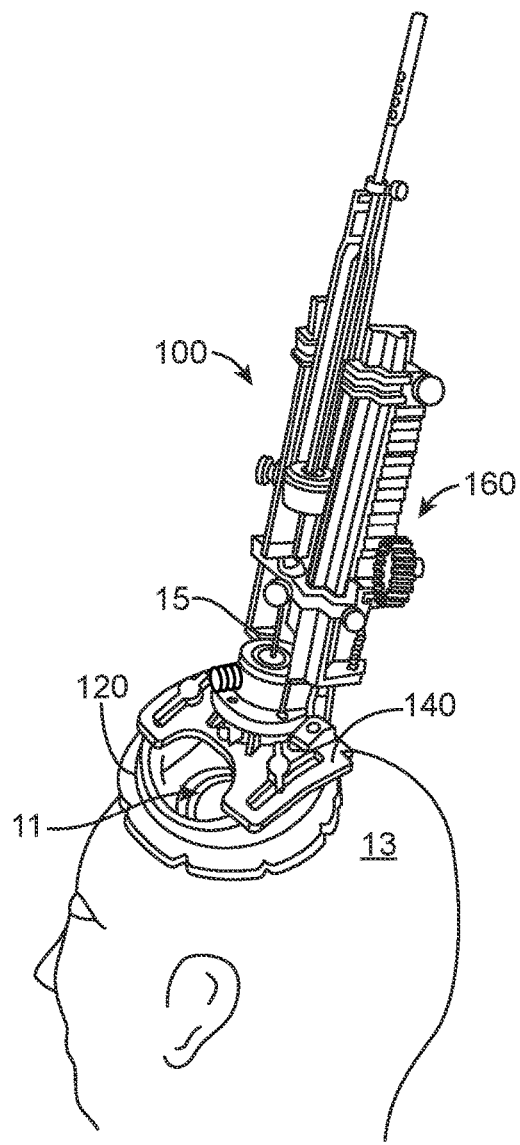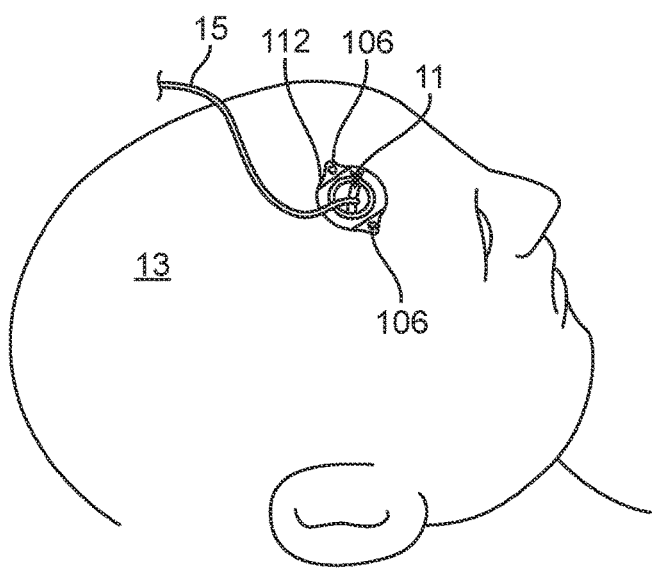
FIG. 1A
FIG. 1B

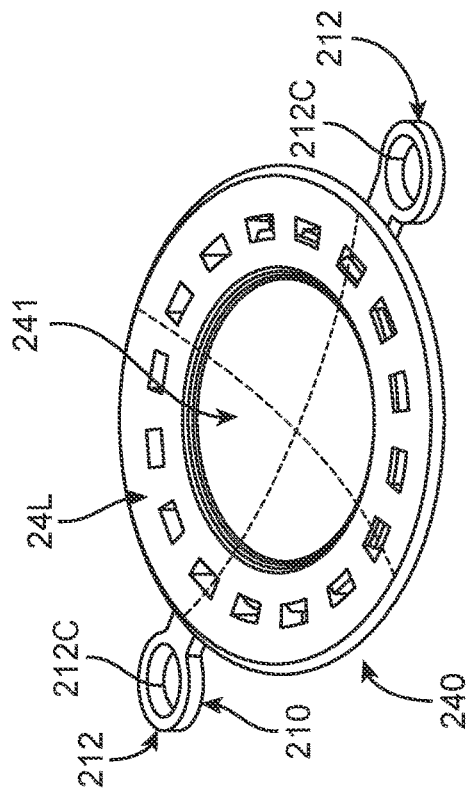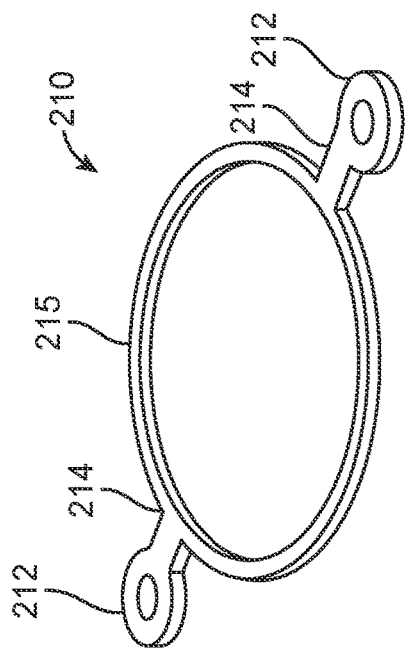
FIG. 2A  FIG. 2B
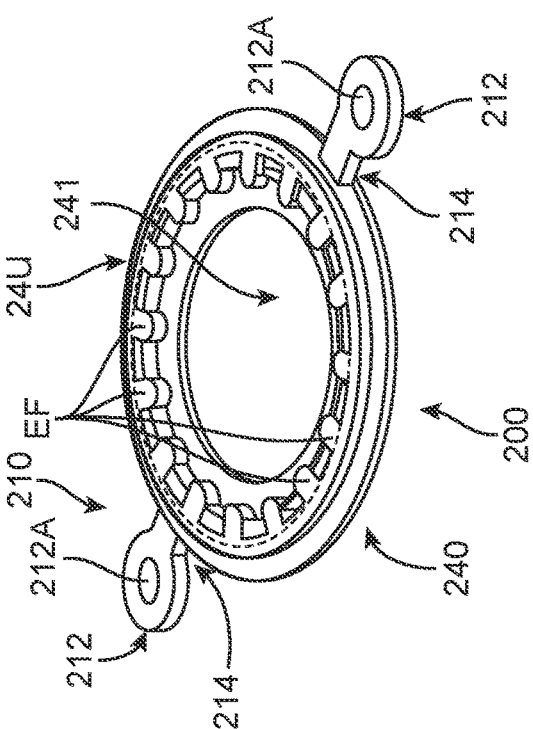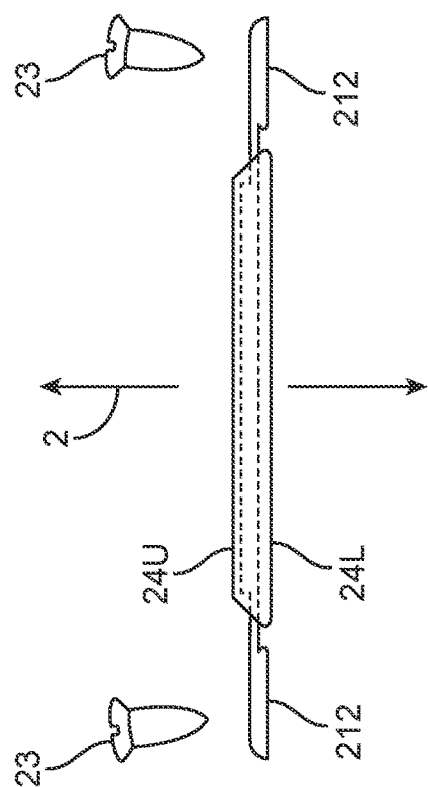
FIG. 2C  FIG. 2D

MEDICAL DEVICE ANCHORING APPARATUS AND PLACEMENT TOOL

CROSS-REFERENCE TO RELATED APPLICATIONS

This application claims the benefit of U.S. Provisional Application No. 62/947,917, filed Dec. 13, 2019, the disclosure of which is incorporated by reference herein in its entirety.

TECHNICAL FIELD

This disclosure generally relates to anchoring medical devices of implantable medical therapy systems, and more particularly to apparatus, tools, and systems that facilitate the anchoring of an elongate portion of the medical device within a body portal, for example, a burr hole formed in a patient's cranium.

BACKGROUND

Medical procedures for treating a variety of neurological conditions, for example, Parkinson's disease, essential tremor, and dystonia, require access to the brain, typically, through a burr hole formed in the cranium, for the insertion of deep brain stimulating electrodes. Burr holes may also be formed for the insertion of a delivery catheter, for example, to provide drug therapy for similar conditions, or an extraction catheter, for example, a hydrocephalus shunt. Stereotactic apparatus and procedures, which are known to those skilled in the art, may be employed by surgeons to locate inserted electrodes and/or drug delivery ports in target regions of the brain.

SUMMARY

The techniques of this disclosure generally relate to an apparatus that is adapted to be fastened to a cranium around a burr hole formed therethrough and a tool that can be utilized to deploy such apparatus. In one or more embodiments, the apparatus can include a base and a cover adapted to connect to the base. The base can include an alignment mark that can be aligned with an alignment mark of the cover such that the cover is oriented in a desired position relative to the base when the cover is connected to the base. Further, in one or more embodiments, the base can include a first lead retaining member and the cover can include a second lead retaining member, where the first and second lead retaining members are adapted to retain a lead when the cover is connected to the base and the lead extends between the first and second lead retaining members.

Further, the present disclosure provides various embodiments of a placement tool for an apparatus to be fastened to a cranium with a fastener around a burr hole formed through the cranium. The tool can include a retainer disposed within a channel of a receptacle that is adapted to hold a fastener. The retainer can include a recess or protrusion adapted to restrain the fastener against movement. Further, the tool can also include an arm that is adapted to align a fastener opening of the apparatus with a channel axis of the channel of the receptacle when the placement tool is engaged with the apparatus.

In one example, aspects of this disclosure relate to a placement tool for an apparatus to be fastened to a cranium with a fastener around a burr hole formed through the cranium. The placement tool includes a receptacle adapted to hold the fastener, where the receptacle includes a channel extending between an upper opening of the receptacle and a lower opening of the receptacle along a channel axis. The placement tool further includes a retainer disposed within the channel of the receptacle, where the retainer includes a recess or a protrusion adapted to restrain the fastener against movement. The fastener opening of the apparatus is configured to align with the channel axis of the channel of the receptacle when the placement tool is engaged with the apparatus.

In another example, aspects of this disclosure relate to an apparatus adapted to be fastened to a cranium around a burr hole formed therethrough. The apparatus includes a base having an orifice, an upper surface, and a lower surface, where the orifice is adapted to be aligned with the burr hole in a direction substantially orthogonal to the cranium. The apparatus further includes a cover adapted to connect to the base and extend over the orifice of the base. The base further includes a first alignment mark and the cover includes a second alignment mark. The first alignment mark is aligned with the second alignment mark in the direction substantially orthogonal to the cranium when the cover is aligned with and connected to the base.

In another example, aspects of this disclosure relate to a method that includes disposing a base on a cranium such that an orifice of the base is substantially aligned in a direction substantially orthogonal to the cranium with a burr hole disposed through the cranium, where the base further includes an upper surface and a lower surface. The method further includes connecting a cover to the base such that a first alignment mark disposed on the base is aligned with a second alignment mark disposed on the cover in the direction substantially orthogonal to the cranium, where the cover occludes the orifice of the base.

In another example, aspects of this disclosure relate to an apparatus adapted to be fastened to a cranium around a burr hole formed therethrough. The apparatus includes a base having an orifice, an upper surface, and a lower surface, where the orifice is adapted to be aligned with the burr hole in a direction substantially orthogonal to the cranium. The apparatus further includes a cover adapted to be connected to the base, where the cover includes an inner surface and a slot adapted to receive a lead of a medical device. The upper surface of the base includes a first lead retaining member and the inner surface of the cover includes a second lead retaining member. The first and second lead retaining members are adapted to retain the lead when the cover is connected to the base and the lead extends between the first and second lead retaining members.

In another example, aspects of this disclosure relate to a placement tool for an apparatus to be fastened to a cranium with a fastener around a burr hole formed through the cranium. The placement tool includes a receptacle adapted to hold the fastener, where the receptacle includes a channel extending between an upper opening of the receptacle and a lower opening of the receptacle along a channel axis. The placement tool also includes a retainer disposed within the channel of the receptacle, where the retainer includes a recess or a protrusion adapted to restrain the fastener against movement. The placement tool further includes an arm extending laterally from the receptacle, where the arm is adapted to align a fastener opening of the apparatus with the channel axis of the channel of the receptacle when the placement tool is engaged with the apparatus. The channel is adapted to align the fastener with a portion of a driving tool when disposed within the channel.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 1A is a schematic perspective view of one embodiment of a stereotactic guidance system mounted to a patient's cranium.

FIG. 1B is a schematic perspective view of one embodiment of an elongate therapy delivery lead or catheter of an implantable medical device extending through an anchoring mechanism after the guidance system has been removed.

FIG. 2A is a perspective view of one embodiment of an apparatus.

FIG. 2B is a perspective view of the apparatus of FIG. 2A.

FIG. 2C is a side view of the apparatus of FIG. 2A.

FIG. 2D is a perspective view of a core of the apparatus of FIG. 2A.

DETAILED DESCRIPTION

Figure 1C:
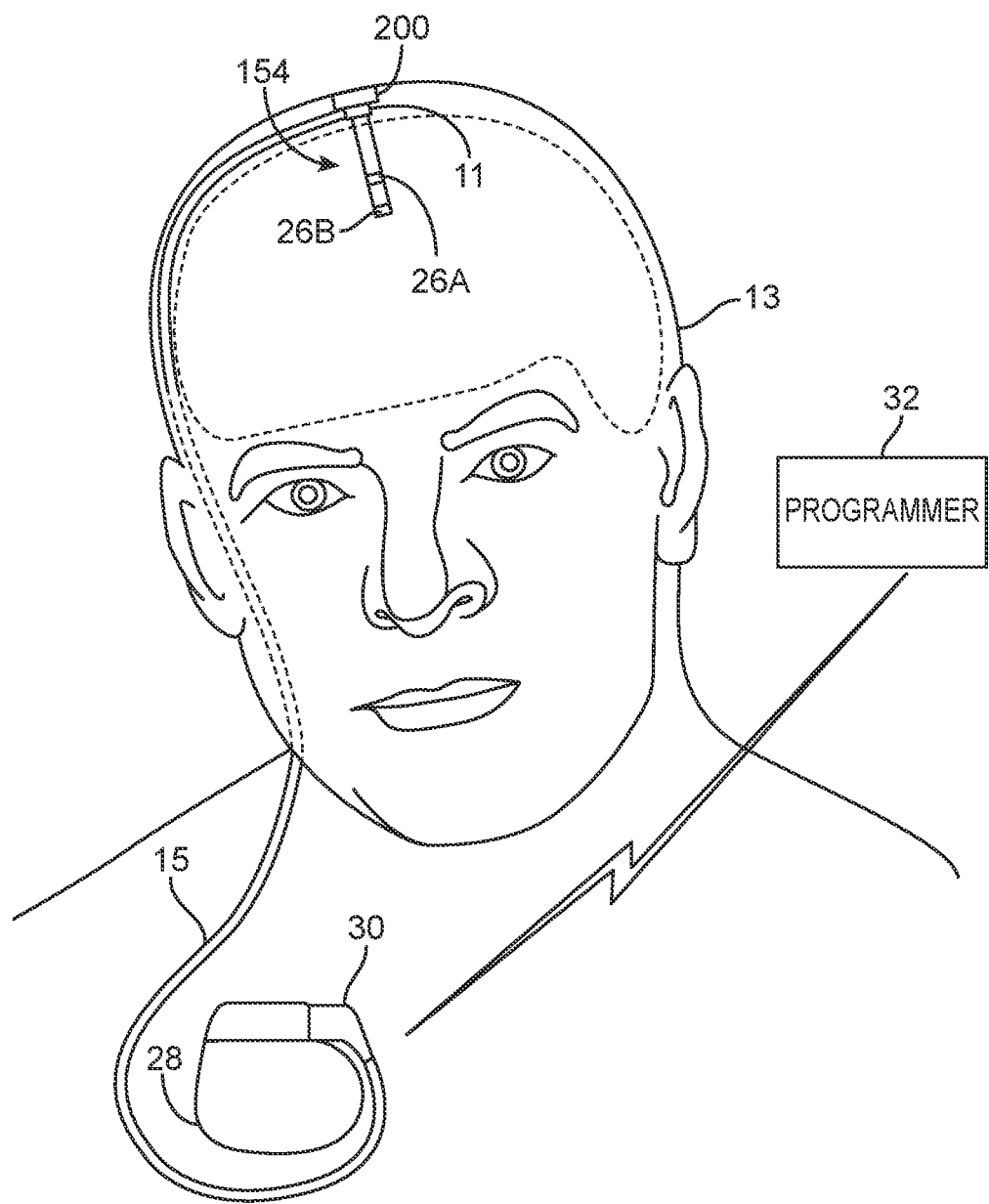
FIG. 1C is a schematic perspective view of one embodiment of an implanted medical therapy system in which various embodiments of the present disclosure can be employed.

The techniques of this disclosure generally relate to an apparatus that is adapted to be fastened to a cranium around a burr hole formed therethrough and a tool that can be utilized to deploy such apparatus. In one or more embodiments, the apparatus can include a base and a cover adapted to connect to the base. The base can include an alignment mark that can be aligned with an alignment mark of the cover such that the cover is oriented in a desired position relative to the base when the cover is connected to the base. Further, in one or more embodiments, the base can include a first lead retaining member and the cover can include a second lead retaining member, where the first and second lead retaining members are adapted to retain a lead when the cover is connected to the base and the lead extends between the first and second lead retaining members.

Further, the present disclosure provides various embodiments of a placement tool for an apparatus to be fastened to a cranium with a fastener around a burr hole formed through the cranium. The tool can include a retainer disposed within a channel of a receptacle that is adapted to hold a fastener. The retainer can include a recess or protrusion adapted to restrain the fastener against movement. Further, the fastener opening of the apparatus is configured to align with a channel axis of the channel of the receptacle when the placement tool is engaged with the apparatus.

Apparatuses that can be placed over a burr hole formed in a cranium of a patient and are adapted to hold a medical device or lead that extends into the cranium typically include a base and a cover. The cover can be oriented in various positions when connected to the base. In some circumstances, however, the cover has a preferred orientation in relation to the base. Such preferred orientation may, however, be difficult to discern, especially when being connected to the base during surgery.

Further, typical apparatuses can include a mechanism that is adapted to retain a lead or medical device that is deployed into the cranium of the patient through the burr hole. Such mechanisms can, however, be cumbersome and unable to prevent the lead from slipping or moving after deployment.

Such apparatuses can also be challenging to connect to the cranium of the patient. Typically, the base of the apparatus includes one or more openings through which a fastener can be threaded or inserted therethrough and into tissue and bone of the patient. The fastener can first be disposed within a receptacle of a placement tool. These fasteners can in some circumstances be quite small, thereby presenting a challenge to the surgeon when attempting to drive them through the base and into the skull. Further, such fasteners tend to be difficult to retain within the tool prior to or as the fastener is driven into the skull by a driving tool.

One or more embodiments of the present disclosure can provide various benefits over typical apparatuses and placement tools. For example, one or more embodiments of an apparatus described herein can include one or more alignment marks disposed on a cover and a base of the apparatus such that the surgeon can more easily connect the cover to the base in the desired orientation. Further, one or more embodiments of an apparatus described herein can include one or more lead retaining members disposed on an inner surface of the cover and an upper surface of the base. The lead retaining members can be adapted to retain a lead when the cover is connected to the base and the lead extends between the lead retaining members. In addition, one or more embodiments of a placement tool described herein can include a retainer disposed within a receptacle of the tool. The retainer can include a recess or protrusion that is adapted to restrain a fastener against movement as the fastener is aligned with a fastener opening of an apparatus.

FIG. 1A is a schematic perspective view showing an exemplary stereotactic guidance system 100 (e.g. Medtronic Nexdrive Micropositioning Drive attached to the Medtronic Nexframe®) mounted to a patient's cranium 13. FIG. 1A illustrates a ring 120 of guidance system 100, which extends around a perimeter of a body portal, or burr hole 11 formed in cranium 13, supporting a socket assembly 140 to which a micropositioning drive 160 is attached. An anchoring mechanism or base 112 (FIG. 1B; e.g., the Medtronic StimLoc®) can be mounted around burr hole 11 and fastened to cranium 13, for example, via fasteners received through fastener openings 106 of a base ring of base 112, prior to attaching ring 120 of guidance system 100. FIG. 1A further illustrates an elongate therapy delivery lead or catheter 15 of a medical device being held within drive 160 for advancement through burr hole 11 and into the cranial space for positioning in a target region of the brain.

FIG. 1B illustrates elongate therapy delivery lead or catheter 15 of the device extending through anchoring mechanism 112, after guidance system 100 has been removed. FIG. 1B further illustrates therapy delivery lead or catheter 15 extending through a slot of mechanism 112 to be anchored between the mechanism and a cap or cover that snaps into place thereover (not shown; e.g., the Medtronic StimLoc® cap). Those skilled in the art appreciate that a proximal length of therapy delivery lead or catheter 15, outside the cranial space, may be routed, beneath the scalp and subcutaneously, to a therapy generator of the device, for example, a generator 28 that is shown, in the schematic of FIG. 1C, implanted subcutaneously in proximity to the patient's clavicle. With further reference to FIG. 1C, a distal length 154 of therapy delivery lead or catheter 15, which has been advanced through burr hole 11, is shown including therapy delivery ports, or electrodes 26A, 26B positioned at the target region.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

FIG. 1C is a schematic showing an implanted medical therapy system in which an apparatus 200 may be employed, according to some embodiments of the present disclosure. FIG. 1C illustrates the system including the aforementioned therapy generator 28 and elongate therapy delivery lead 15, also referred to herein generally as a therapy delivery device, which is shown coupled thereto via a connector 30 that terminates the proximal length thereof. In other examples, the therapy delivery device may be a catheter. According to an exemplary embodiment, therapy generator 28 is configured to deliver electrical stimulation therapy to, and/or sense electrical signals from the patient's brain, via lead electrodes 26A, 26B that are mounted to distal length 154 of lead 15 and electrically coupled to connector 30 via insulated conductors. Those skilled in the art are familiar with suitable configurations and constructions for lead 15 and generator 28. Therapy generator 28 can include processing circuitry, memory, signal generation circuitry, sensing circuitry, telemetry circuitry, and a power source, where the memory can include computer-readable instructions that are executed by the processing circuitry, for example, to deliver stimulation therapy to the patient, sense physiological signals of the patient, and/or perform other functions related to treating one or more conditions of the patient. The telemetry circuitry may include any suitable hardware, firmware, software or any combination thereof for communicating with another device, such as a programmer 32. Under the control of the processing circuitry the telemetry circuitry can receive downlink telemetry from and send uplink telemetry to programmer 32 with the aid of an antenna, which may be internal and/or external. Programmer 32 may be a handheld computing device, computer workstation, or networked computing device that includes electronics and other internal components necessary or desirable for executing the functions associated with the system.

FIG. 1C further illustrates lead distal length 154 extending through an apparatus 200, which is fastened to the patient's cranium 13 around the above-described burr hole 11. According to embodiments described herein, apparatus 200 is configured to receive attachment thereto a medical device anchoring mechanism that secures lead 15 in place so that electrodes 26A, 26B remain positioned at the aforementioned target regions of the patient's brain for stimulation thereof over the course of the system implant.

FIGS. 2A-B are perspective views of apparatus 200; and FIG. 2C is an elevation view of apparatus 200. FIGS. 2A-C illustrate apparatus 200 including a substantially flat core 210 and a shell or base 240, and FIG. 2D shows, in perspective view, core 210 without shell 240. FIG. 2D illustrates core 210 including a ring portion 215 and first and second pliable arms 214 extending laterally from ring portion 215, wherein each of first and second fastener members 212 of core 210 terminate a corresponding pliable arm 214. FIGS. 2A-C further illustrate shell 240 encapsulating ring portion 215. Ring portion 215 is indicated with dashed lines in FIGS. 2A and 2C. Shell 240 defines an orifice 241 of apparatus 200, which is substantially centered within ring portion 215 of core 210. In FIG. 2B, dashed lines accentuate a curved contour of a lower surface 24L of shell 240, to match a curvature of the patient's cranium (e.g. cranium 13 of FIGS. 1A-C). But core 210, being substantially flat, extends within shell 240 without such a curvature. Core 210 can include any suitable material or materials, e.g., a medical grade titanium that is machined. Further, shell 240 can include any suitable material or materials, e.g., a medical grade polymer, such as polysulfone or polyether ether ketone (PEEK), that can be insert molded around core 210. In one or more embodiments, the curvature of shell lower surface 24L corresponds to an approximately ten inch diameter cranium, and a nominal maximum thickness between upper surface 24U and lower surface 24L may be approximately 0.05 inches.

Figure 2E:
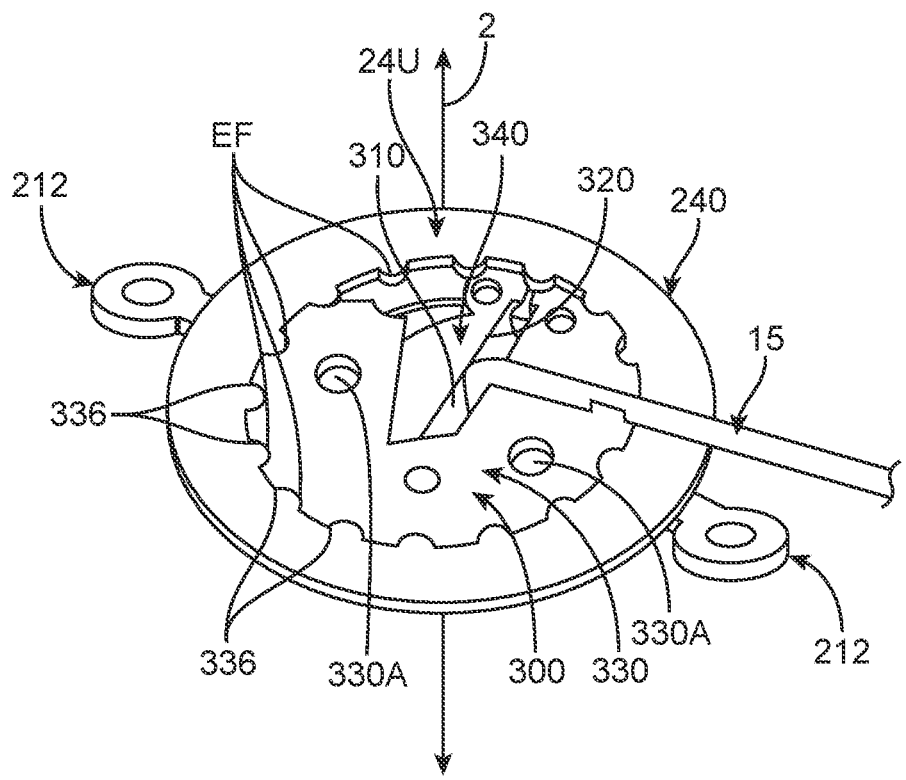
FIG. 2E is a perspective view of an anchoring mechanism connected to the apparatus of FIG. 2A.
Figure 2F:
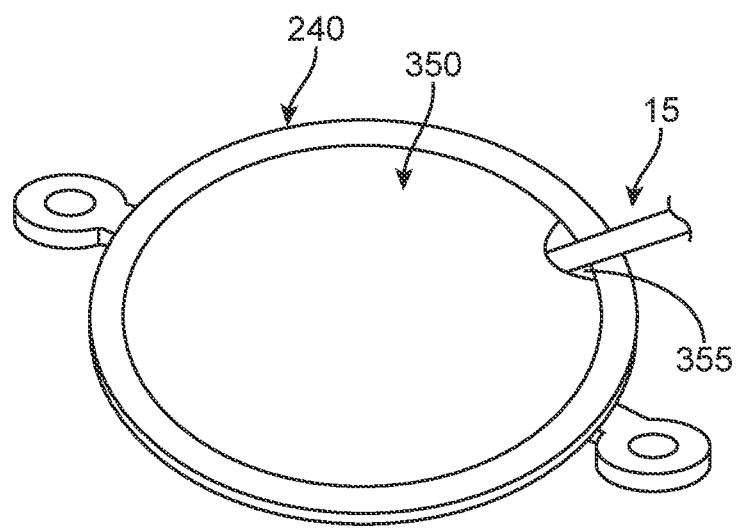
FIG. 2F is a perspective of the anchoring mechanism of FIG. 2E.

With further reference to FIG. 2A, an upper surface 24U of apparatus shell or base 240 defines a rim that has a plurality of uniform engagement features EF formed therein, which are equally spaced apart from one another around an entire perimeter of the rim. Engagement features EF can be adapted to receive attachment of the aforementioned medical device anchoring mechanism that secures a portion of the implanted medical device in place, for example, elongate therapy delivery lead 15 (FIGS. 1A-C). Such an anchoring mechanism is described in co-pending and commonly assigned U.S. Provisional Patent Applications having Ser. Nos. 62/400,140 and 62/446,923, salient portions of which are hereby incorporated by reference. FIG. 2E is a perspective view of a clip or jaw 300 of such an anchoring mechanism seated against shell upper surface 24U of apparatus 200. FIG. 2E illustrates jaw 300 including a plurality of uniform interlocking features 336 formed in an outer perimeter edge of a first plate member 330 thereof, which interlock with engagement features EF of apparatus 200. FIG. 2E further illustrates first plate member 330 of jaw 300 including a sidewall 310 that has a gripping surface opposing that of a sidewall 320 of a second plate member 340 of jaw 300, where second plate member 340 is movable relative to first plate member 330 to open and close jaw 300. In FIG. 2E, jaw 300 is shown closed and gripping the implanted lead 15 between grip surfaces of sidewalls 310, 320. The uniformity of form and spacing of apparatus engagement features EF and jaw interlocking features 336 allow the operator to seat jaw 300 in a plurality of orientations about a longitudinal axis 2 of apparatus 200, for example, to accommodate a trajectory of the implanted lead 15 through burr hole 11. FIG. 2F is a perspective view of a cap 350 of the anchoring mechanism covering jaw 300 and including a channel 355 through which the anchored lead 15 passes. According to some embodiments, for example, like those described in the aforementioned co-pending and commonly assigned U.S. Provisional Patent Application Ser. Nos. 62/400,140 and 62/446,923, cap or cover 350 includes studs that project from a lower surface thereof and are configured to mate in a press fit with apertures 330A (FIG. 2E) of jaw plate member 330.

Figure 3:
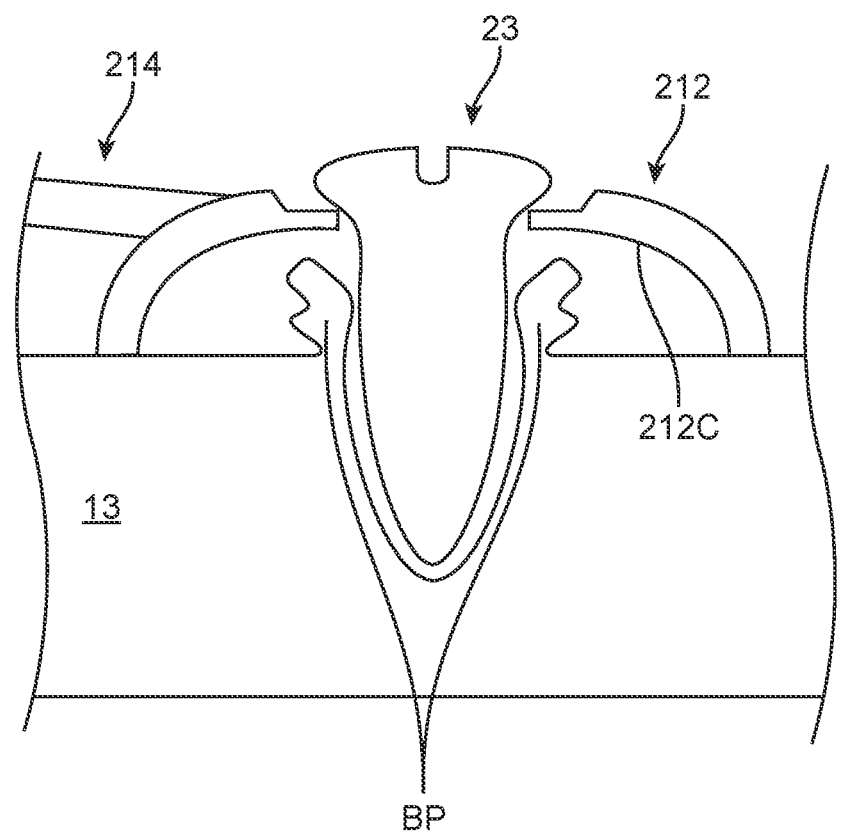
FIG. 3 is a schematic cross-section view of a portion of the apparatus of FIG. 2A fastened to the patient's cranium.

With further reference to FIGS. 2B-C, each fastener member 212 of apparatus core 210 has an aperture or fastener opening 212A to receive extension of a bone screw 23 therethrough for fastening apparatus 200 to the patient's cranium 13 when apparatus orifice 241 has been centered over cranial burr hole 11, for example, as described below in conjunction with FIGS. 4A-C. When each bone screw 23 is positioned through the corresponding fastener member 212 of the centered apparatus 200 and driven into cranium 13, for example as illustrated in the schematic cross-section of FIG. 3, each pliable arm 214 of core 210 may bend from the relaxed substantially flat form of core 210 to generally conform to the curvature of cranium 13. FIG. 3 further illustrates cranial bone material BP, which has been displaced by the driven bone screw 23, piled up in a pillar-like formation that surrounds screw 23. Because the displaced bone material BP is relatively hard and firm, and remains attached to cranium 13, unless some clearance between fastener member 212 and cranium 13 is provided, the fastened apparatus 200 may rock, or wiggle, and not provide a stable base for the aforementioned medical device anchoring mechanism. Thus, according to preferred embodiments, and with reference to FIGS. 2B and 3, each fastener member 212 of apparatus has a concave surface 212C facing in a same direction as lower surface 24L of shell 240 to provide clearance for displaced bone material BP. The fastener openings 212A of each fastener member 212 are shown extending through an apex of the corresponding concave surface 212C. It should be noted that, according to some alternate embodiments, core 210 of apparatus 200 can include more than two pliable arms 214 and corresponding fastener members 212.

Figure 4:
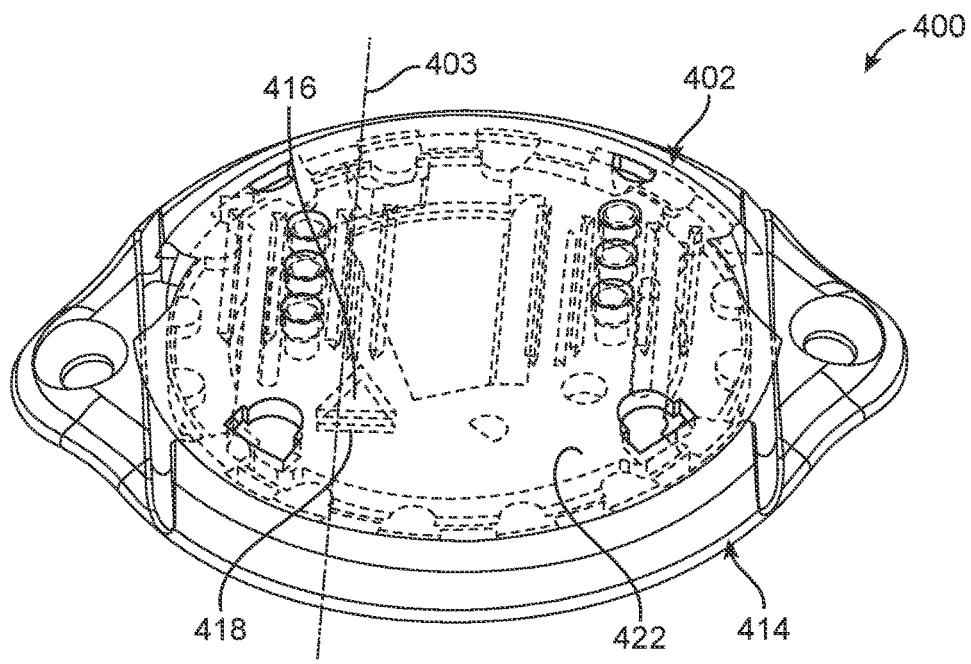
FIG. 4 is a schematic perspective view of another embodiment of an apparatus.
Figure 5:
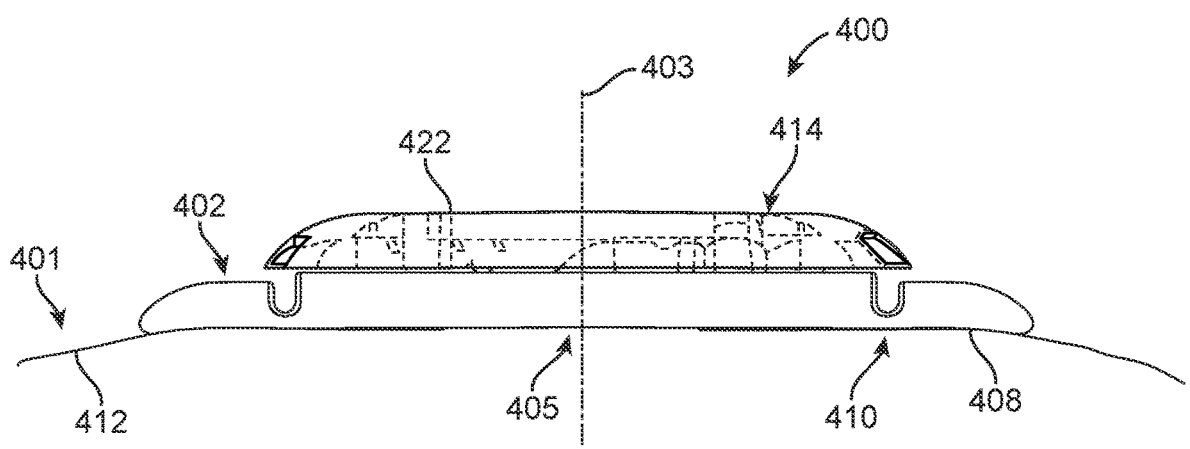
FIG. 5 is a schematic side view of the apparatus of FIG. 4 disposed on a cranium of a patient.
Figure 6:
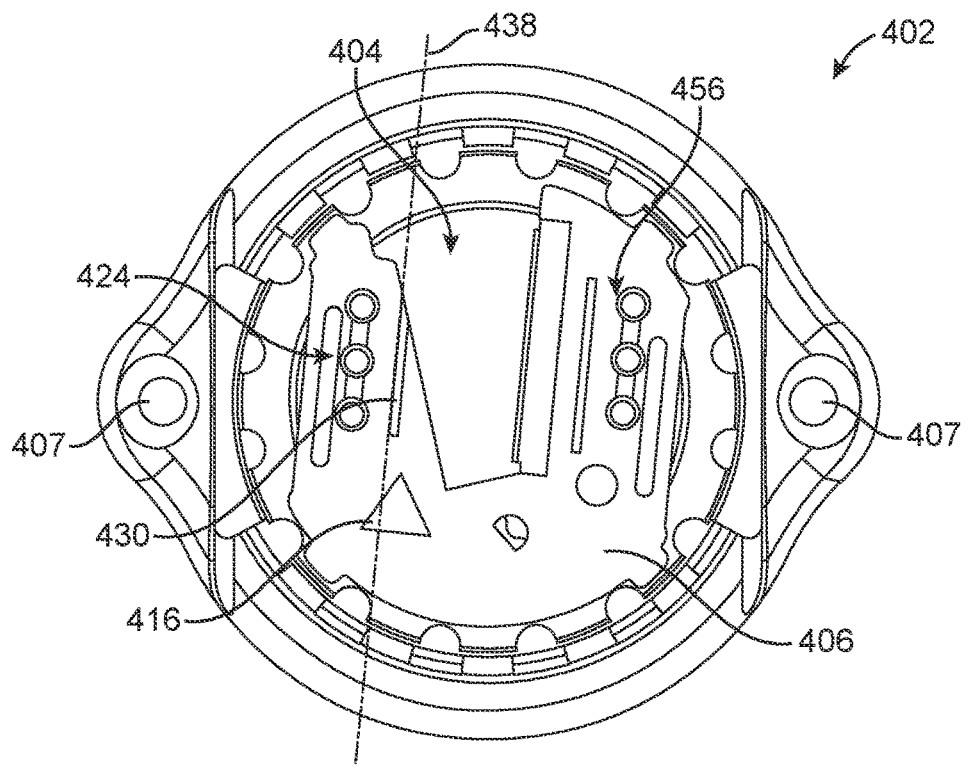
FIG. 6 is a schematic plan view of a base of the apparatus of FIG. 4.

The various embodiments of apparatuses described herein can include one or more alignment marks to assist in orientating a cover of the apparatus with the base. For example, FIGS. 4-6 are various views of one embodiment of an apparatus 400. All of the design considerations and possibilities regarding the apparatus 200 of FIGS. 2A-3 apply equally to the apparatus 400 of FIGS. 4-6. The apparatus 400 can be adapted to be fastened to a cranium 401 around a burr hole 405 formed therethrough. The apparatus 400 includes a base 402 (FIG. 6) having an orifice 404, an upper surface 406, and a lower surface 408. The orifice 404 is adapted to be aligned with the burr hole 405 in a direction 403 substantially orthogonal to the cranium 401 as can be seen, e.g., in FIG. 5. Further, in one or more embodiments, the lower surface 408 can include a contour 410 that substantially matches a curvature 412 of the cranium 401 around the burr hole 405 as shown in FIG. 5. As used herein, the term "substantially matches" means that a gap between the lower surface 408 and the cranium 401 is no greater than 10 mm. In one or more embodiments, the term "substantially matches" means that the lower surface 408 generally conforms to the curvature 412 of the cranium 401. The apparatus 400 can also include a cover 414 adapted to connect to the base 402 and extend over the orifice 404 of the base.

The base 402 further includes a first alignment mark 416 and the cover 414 includes a second alignment mark 418. The first alignment mark 416 is aligned with the second alignment mark 418 in the direction 403 substantially orthogonal to the cranium 401 when the cover 414 is aligned with and connected to the base 402. Although depicted as including two alignment marks 416, 418, the apparatus 400 can include any suitable alignment marks disposed in any suitable portion or portion of the base 402 and the cover 414.

The base 402 can take any suitable shape or shapes and have any suitable dimensions. Further, the base 402 can include any suitable material or materials. The base 402 can be connected to the cranium 401 using any suitable technique or techniques. In one or more embodiments, the base 402 can be connected to the cranium 401 by one or more fasteners (e.g., fastener 23 of FIG. 3) that are disposed through fastener openings 407 formed between the upper surface 406 and the lower surface 408 of the base 402.

The cover 414, which is adapted to connect to the base 402, can take any suitable shape or shapes and have any suitable dimensions. Further, the cover 414 can include any suitable material or materials. In one or more embodiments, the cover 414 is substantially transparent such that the first alignment mark 416 of the base 402 is visible through the cover when the cover is connected to the base. As used herein, the term "substantially transparent" means that the cover of the apparatus transmits greater than 50% of electromagnetic radiation incident on the substrate for a selected wavelength or range of wavelengths, assuming no reflection at the air-substrate boundaries. The cover 414 can include any suitable materials such that it is substantially transparent, e.g., plastic, nylon, silicone, etc.

The first alignment mark 416 can be disposed in any suitable location on the base 402. In one or more embodiments, the first alignment mark 416 can be disposed on the upper surface 406 of the base 402. In one or more embodiments, the base 402 can be substantially transparent, and the first alignment mark 416 can be disposed on the lower surface 408. In such embodiments, the first alignment mark 416 can be visible through the base 402.

Further, the second alignment mark 418 can be disposed in any suitable location on the cover 414. In one or more embodiments, the second alignment mark 418 can be disposed on an inner surface 420 of the cover 414. In one or more embodiments, the second alignment mark 418 can be disposed on an outer surface 422 of the cover 414.

Although depicted as including triangular shapes, the first and second alignment marks 416, 418 can include any suitable mark, e.g., at least one of an indicium, a protrusion, a recess, one or more lines, one or more geometric shapes (e.g., rectangular, ovular, triangular), an icon, an image, or a color. In one or more embodiments, the first alignment mark 416 is the same as the second alignment mark 418. In one or more embodiments, the first alignment mark 416 is different from the second alignment mark 418.

The first and second alignment marks 416, 418 can be disposed on the base 402 and the cover 414 using any suitable technique or techniques. In one or more embodiments, at least one of the first and second alignment marks 416, 418 can be formed separate from the respective base 402 and cover 414 and connected to the base or cover using any suitable technique or techniques. In one or more embodiments, at least one of the first or second alignment marks 416, 418 can be integral with the respective base 402 and cover 414. In such embodiments, the alignment marks 416, 418 can be formed using any suitable technique or techniques, e.g., molding, embossing, etching, etc.

In one or more embodiments, at least one of the first or second alignment marks 416, 418 can include one or more colors. For example, the first alignment mark 416 can include a first color and the second alignment mark 418 can include a second color. The first color and the second color can combine to provide a third color to a user viewing the outer surface 422 of the cover 414 when the first alignment mark is aligned with the second alignment mark. For example, the first alignment mark 416 can be blue and the second alignment mark 418 can be yellow. The two alignment marks 416, 418 would, therefore, combine to provide a green color that indicates to the user that the first alignment mark is aligned with the second alignment mark along the axis 403.

Further, each of the alignment marks 416, 418 can be selected such that when aligned form a shape that is different from the shapes of each of the alignment marks. The formation of a new shape can indicate to the user that the first and second alignment marks 416, 418 are aligned and the cover 414 is in the desired orientation relative to the base 402. For example, the first alignment mark 416 can include a triangular shape and the second alignment mark 418 can include a triangular shape that is rotated about a normal to the upper surface 406 of the base. The first shape and the second shape can combine to form a star shape as viewed by the user when viewing the outer surface 422 of the cover 414 when the first alignment mark 416 is aligned with the second alignment mark 418 and the cover is connected to the base 402.

As mentioned herein, the first and second alignment marks 416, 418 can include one or more protrusions or recesses. In one or more embodiments, the first alignment mark 416 can include a protrusion disposed on the upper surface 406 of the base 402 and the second alignment mark 418 can include a recess disposed on the inner surface 420 of the cover 414. The second alignment mark 418 is adapted to engage the first alignment mark 416 when the cover 414 is connected to the base 402 such that the first and second alignment marks fit into place, thereby indicating to the user that the cover is oriented in the desired position relative to the base. In one or more embodiments, the first alignment mark 416 can include a recess disposed on the upper surface 406 of the base 402 and the second alignment mark 418 can include a protrusion disposed on the inner surface 420 of the cover 414. The first alignment mark 416 is adapted to engage the second alignment mark 418 when the cover 414 is connected to the base 402. Each of the first and second alignment marks 416, 418 can include one or more protrusions or recesses that take any suitable shape or shapes.

Figure 12:
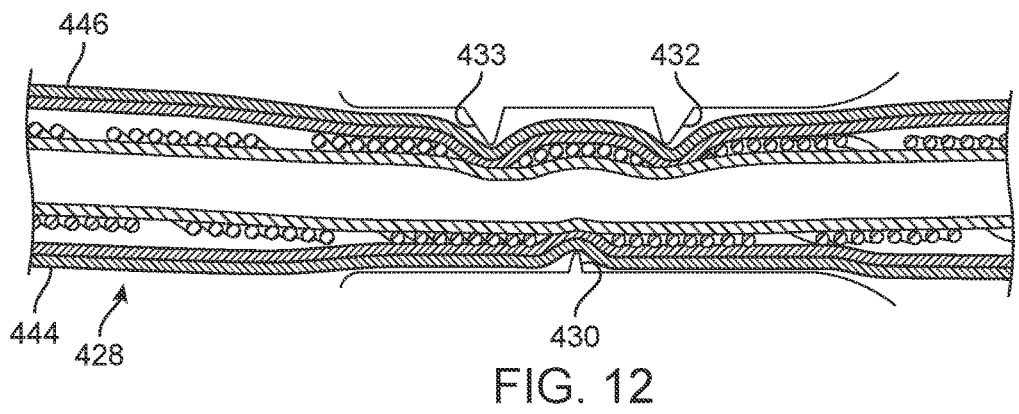
FIG. 12 is a schematic cross-section view of the portion of the portion of the apparatus of FIG. 11.
Figure 13:
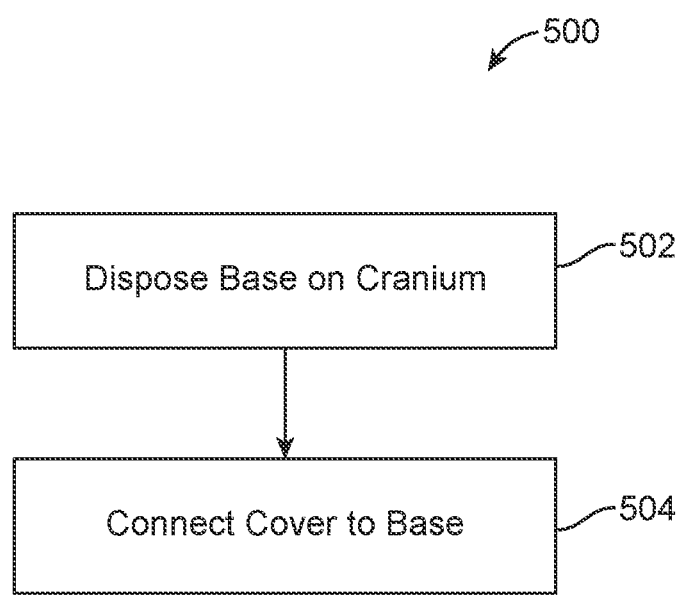
FIG. 13 is a flow chart of one method of disposing the apparatus of FIG. 4 on the cranium of the patient.
Figure 14:
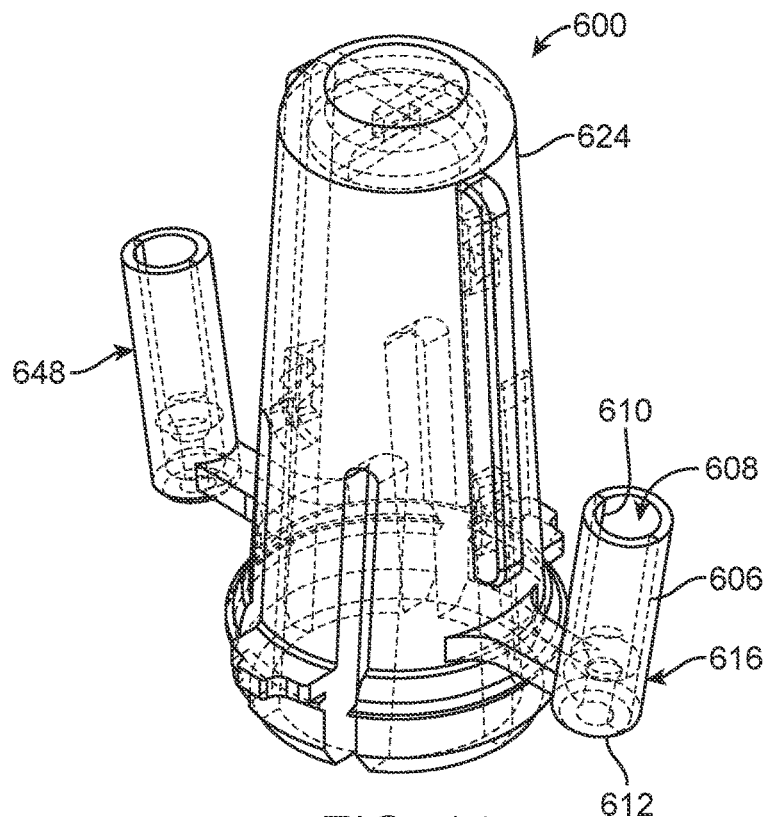
FIG. 14 is a schematic perspective view of one embodiment of a placement tool.
Figure 15:
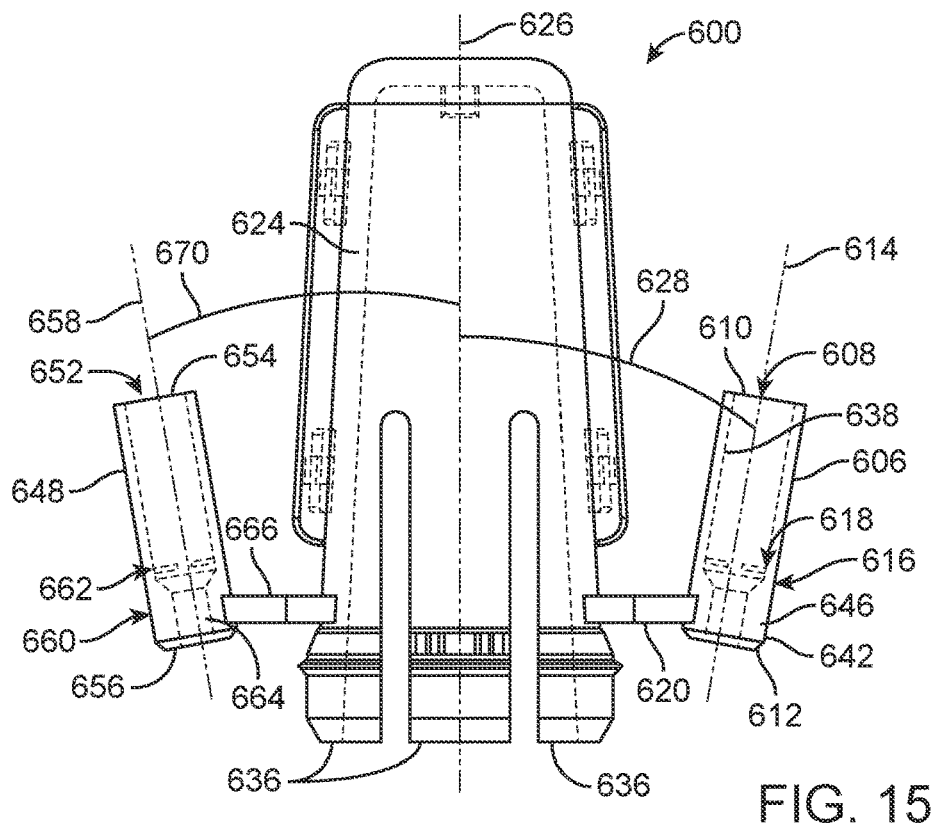
FIG. 15 is a schematic side view of the placement tool of FIG. 14.
Figure 16:
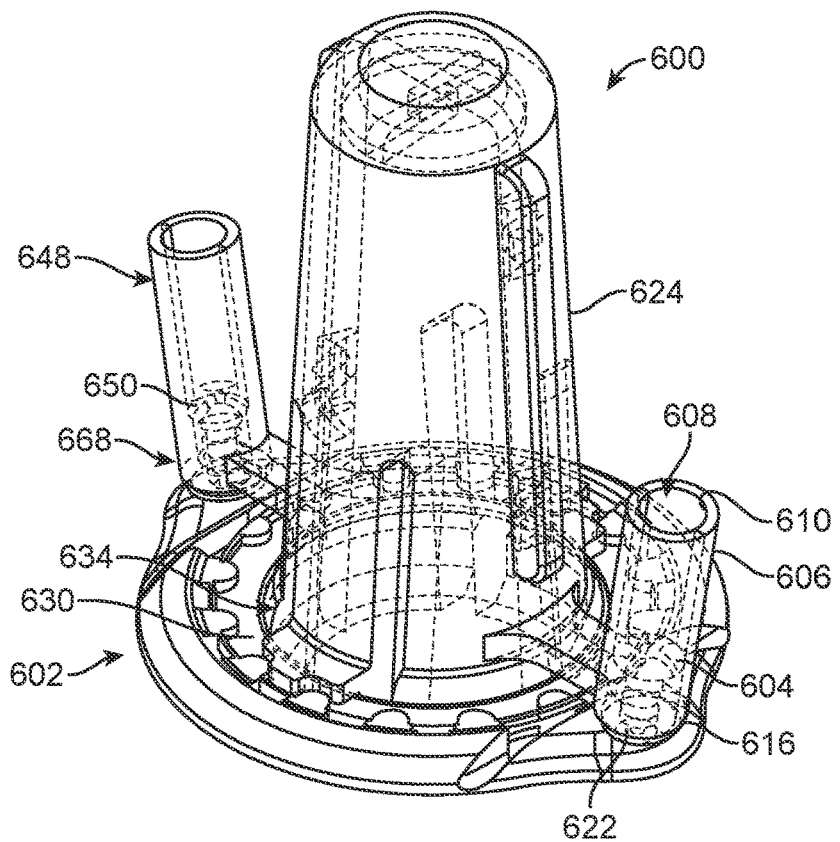
FIG. 16 is a schematic perspective view of the placement tool of FIG. 14 engaged with an apparatus.
Figure 17:
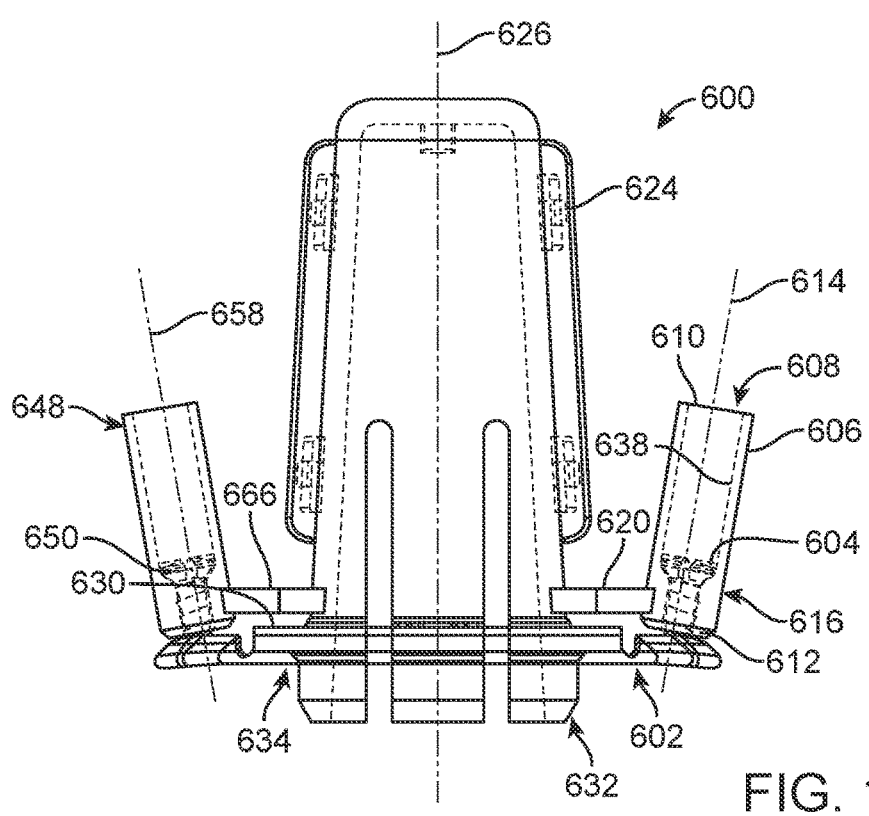
FIG. 17 is a schematic side view of the placement tool and apparatus of FIG. 16.

Any suitable technique or techniques can be utilized to dispose the cover 414 onto the base 402 such the first and second alignment marks 416, 418 are aligned. For example, FIG. 13 is a flowchart of one method 500 of connecting the cover 414 to the base 402. Although described in regard to apparatus 400 of FIGS. 4-12, the method 500 can be utilized with any suitable apparatus.

At 502, the base 402 is disposed on the cranium 401 such that the orifice 404 of the base is substantially aligned in a direction substantially orthogonal to the cranium with the burr hole 405 disposed through the cranium. In one or more embodiments, a core (e.g., core 210 of FIG. 2A) can be fastened to the cranium around the burr hole 405 prior to disposing the base 402 on the cranium 401, where the base 402 encapsulates a ring portion (e.g., ring portion 215 of FIG. 2D) of the core that surrounds the burr hole when the base is disposed on the cranium. The cover 414 can be connected to the base 402 such that the first alignment mark 416 disposed on the base is aligned with the second alignment mark 418 disposed on the cover in the direction substantially orthogonal to the cranium 401 at 504, where the cover occludes the orifice 404 of the base at 506.

Figure 7:
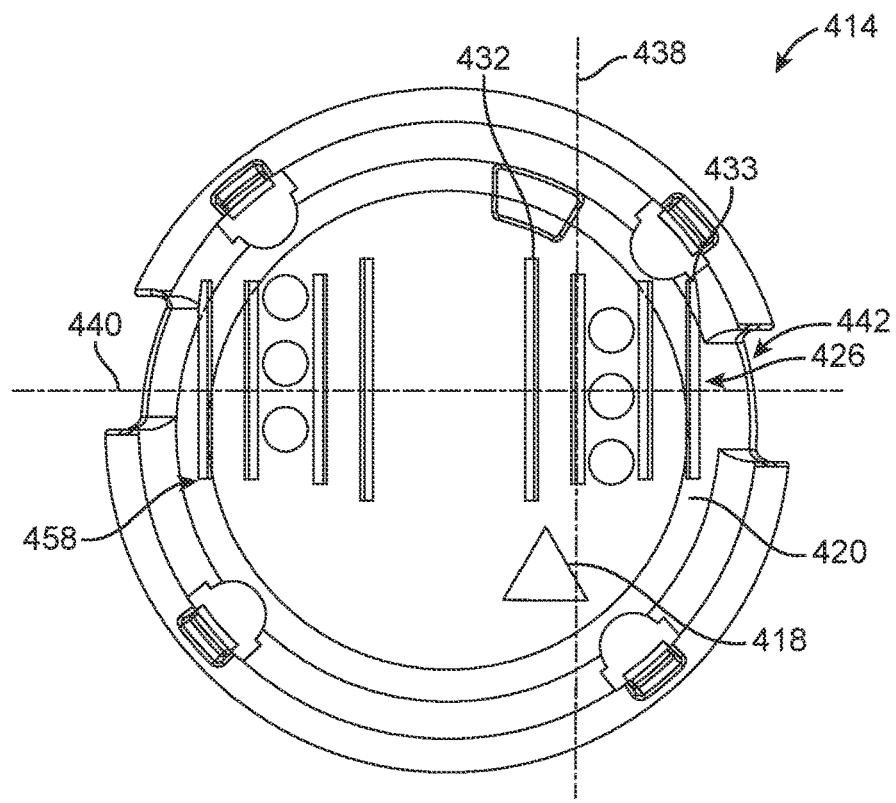
FIG. 7 is a schematic plan view of a cover of the apparatus of FIG. 4.
Figure 8:
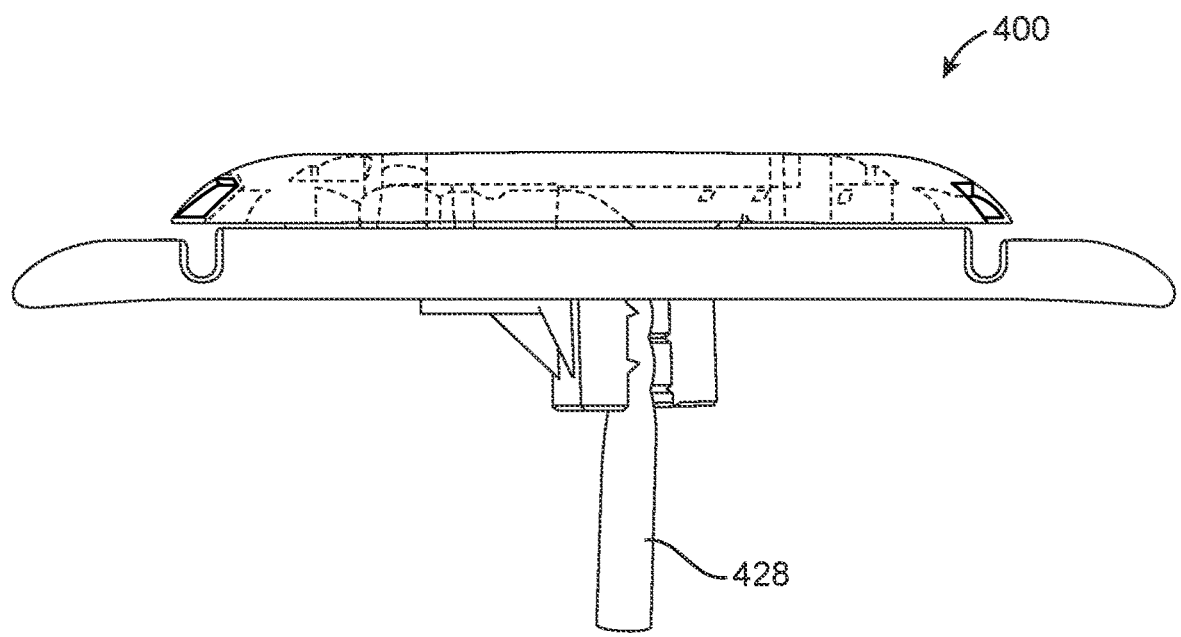
FIG. 8 is a schematic side view of the apparatus of FIG. 4 and a lead extending through the base.
Figure 9:
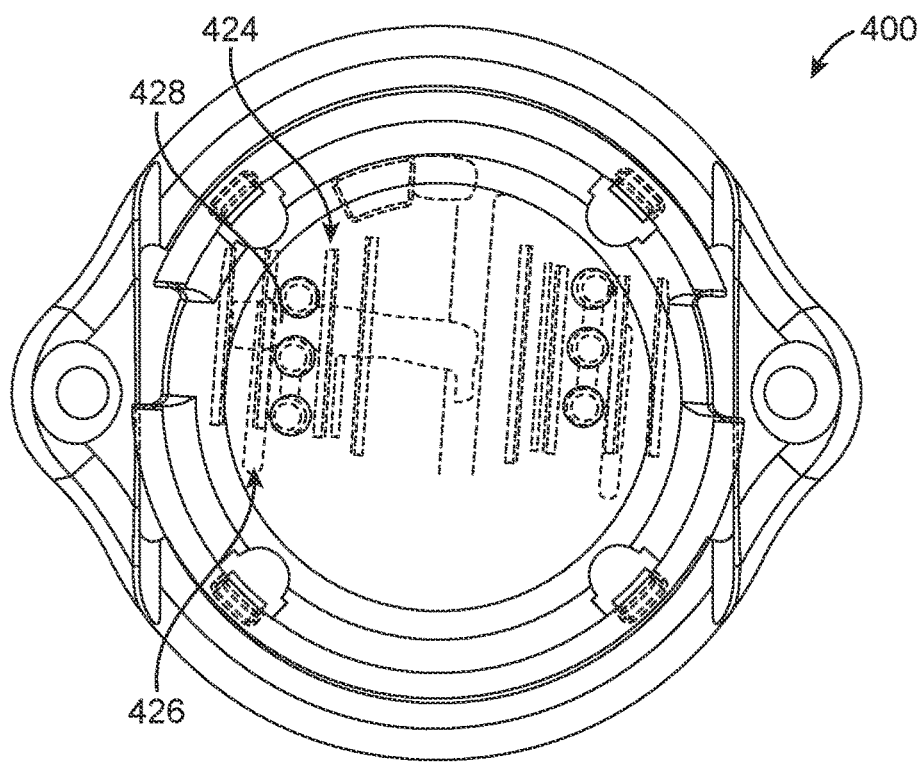
FIG. 9 is a schematic perspective view of the apparatus of FIG. 4.

As mentioned herein, the various embodiments of apparatuses can include one or more lead retaining members for retaining a lead or medical device that has been disposed within the cranium through burr hole. For example, as shown in FIGS. 6-7, the upper surface 406 of the base 402 includes a first lead retaining member 424, and the inner surface 420 of the cover 414 includes a second lead retaining member 426. The first and second lead retaining members 424, 426 are adapted to retain a lead 428 (FIG. 9) when the cover 414 is connected to the base 402 and the lead extends between the first and second lead retaining members as shown in FIGS. 9-12. In one or more embodiments, the first and second lead retaining members 424, 426 are adapted to retain at least two leads when the cover 414 is connected to the base 402 and each of the at least two leads extend between the first and second lead retaining members. The leads can include any suitable lead or leads, e.g., lead wires, lead circuits, lead members, etc. The first and second lead retaining members 424, 426 can be adapted to retain any suitable number of leads.

The apparatus 400 can include at least first and second lead retaining members 424, 426 and one or more alignment marks 416, 418. In one or more embodiments, the apparatus 400 can include one or more alignment marks 416, 418 and no lead retaining members. Further, in one or more embodiments, the apparatus 400 can include at least first and second lead retaining members 424, 426 and no alignment marks.

The first and second lead retaining member 424, 426 can include any suitable elements or components that can be adapted to retain the lead 428. For example, the first lead retaining member 424 includes protrusion 430, and the second lead retaining member 426 includes a first protrusion 432 and a second protrusion 433. The protrusions 430, 432, 433 can take any suitable shape or shapes and have any suitable dimensions. As shown in FIGS. 6-12, the protrusions 430, 432, 433 of each of the first and second lead retaining members 424, 426 include one or more elongated teeth that have a substantially triangular cross-section in a plane orthogonal to the inner surface 420 of the cover 414 and the upper surface 406 of the base 402 respectively, i.e., in the plane of FIGS. 10-12. The protrusion 430 of the first lead retaining member 424 and the protrusions 432, 433 of the second lead retaining member 426 can have the same shape. In one or more embodiments, each of the protrusions 430, 432, 433 can take a unique shape. Further, each of the first and second lead retaining members 424, 426 can have any suitable number of protrusions 430, 432, 433. In one or more embodiments, each of the first lead retaining member 424 and the second lead retaining member 426 can have a protrusion 430, 432, 433 that is different from another protrusion of respective member.

The protrusions 430, 432, 433 can be oriented in any suitable arrangement relative to the lead 428, the base 402, and the cover 414. In one or more embodiments, each protrusion 430, 432, 433 extends along a gripping axis 438 that is substantially orthogonal to a slot axis 440 of a slot 442 of the cover 414 when the cover is connected to the base 402. The slot 442 of the cover 414 is adapted to allow the lead 428 to extend therethrough and beyond the cover and the base 402. As used herein, the term "substantially orthogonal" means that the slot axis 440 forms an angle with the gripping axis 438 that is at least 85 degrees and no greater than 95 degrees. In one or more embodiments, at least one of the protrusions 430, 432, 433 can extend along an axis that forms an angle with an axis of another protrusion.

Further, the first lead retaining structure 424 can be disposed in any suitable location on the upper surface 406 of the base 402, and the second lead retaining structure 426 can be disposed in any suitable location on the inner surface 420 of the cover 414. Although depicted as having one lead retaining member 424, the base 402 can include any suitable number of lead retaining structures. Further, the cover 414 can also include any suitable number of lead retaining members.

For example, the upper surface 406 of the base 402 includes a third lead retaining member 456 (FIG. 6) disposed such that the orifice 404 is disposed between the first lead retaining member 424 and the third lead retaining member. Further, the inner surface 420 of the cover 414 includes a fourth lead retaining member 458 (FIG. 7), where the third lead retaining member 456 and fourth lead retaining member are adapted to retain the lead 428 of the medical device when the cover is connected to the base 402 and the lead extends between the third and fourth lead retaining members. The third and fourth lead retaining members 456, 458 can include any suitable protrusions, e.g., the same protrusions described herein regarding the first and second lead retaining members 424, 426.

Figure 10:
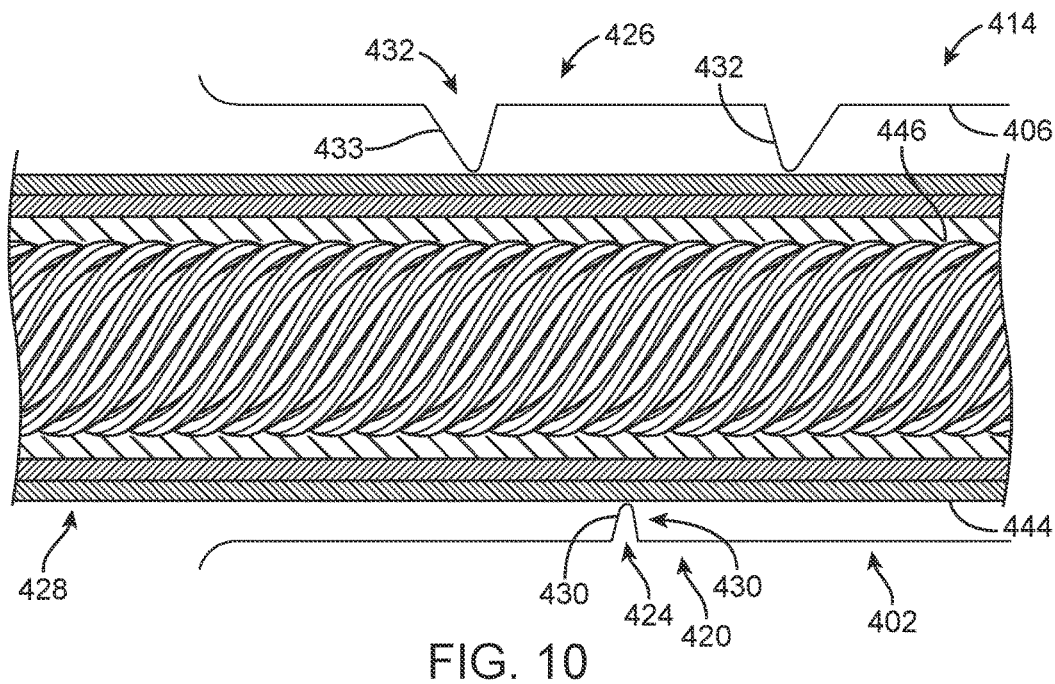
FIG. 10 is a schematic cross-section view of a portion of the apparatus of FIG. 4 and the lead disposed between lead retaining members of the cover and the base.
Figure 11:
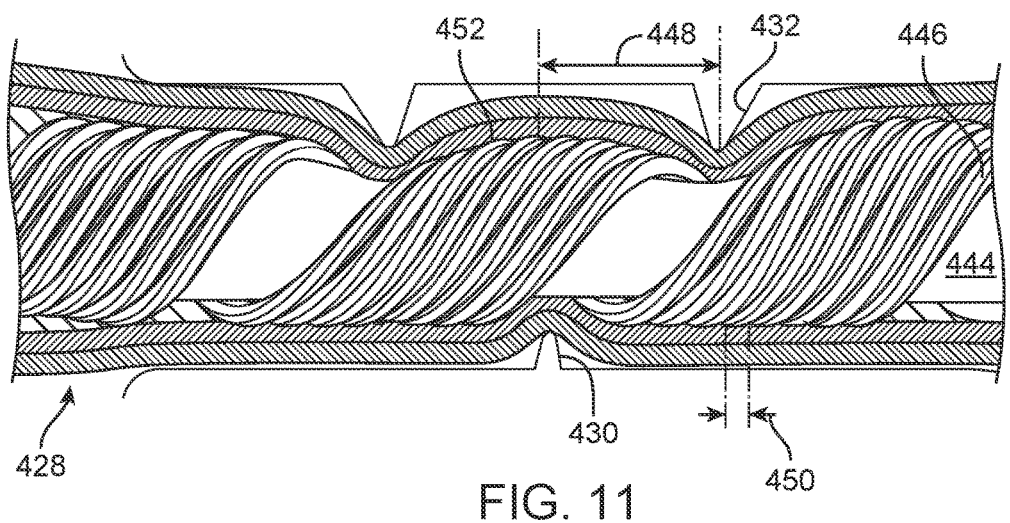
FIG. 11 is a schematic cross-section view of the portion of the apparatus of FIG. 10 with the lead retaining members of the cover and base retaining the lead.

The protrusion 430 of the first lead retaining member 424 can be disposed in any suitable relationship relative to the protrusions 432, 433 of the second lead retaining member 426. For example, as shown in FIGS. 10-12, the protrusion 430 of the first lead retaining member 424 is adapted to engage the lead 428, and the protrusions 432, 433 of the second lead retaining member 426 are laterally spaced apart from the protrusion of the first lead retaining member when the cover 414 is connected to the base 402. The protrusions 432, 433 of the second lead retaining member 426 are also adapted to engage the lead 428 of the medical device.

The lead 428 that is retained by the first and second lead retaining members 424, 426 can have any suitable structure and include any suitable material or materials. As shown in FIGS. 10-12, the lead 428 includes an elongated body 444 and a conductor 446 wound around the elongated body. The elongated body 444 can include any suitable dielectric material or materials, and the conductor 446 can include any suitable conductive materials.

As can be seen in FIG. 11, the protrusions 430, 432, 433 of the first and second lead retaining members 424, 426 are adapted to displace the conductor 446 to retain the lead 428 when the cover 414 is connected to the base 402. In one or more embodiments, a lateral spacing 448 between the protrusion 430 of the first lead retaining member 424 and a protrusion 432 of the second lead retaining member 426 that is provided when the cover 414 is connected to the base 402 can be any suitable distance. In one or more embodiments, such lateral spacing 448 is equal to no greater than eight times a diameter 450 of the conductor 446 as shown in FIG. 11, such that at least two windings 452 of the conductor are disposed between the protrusion 430 of the first lead retaining member 424 and one protrusion 432 of the second lead retaining member when the first and second lead retaining members are engaged with the elongated body 444 of the lead 428 of the medical device. In one or more embodiments, at least four windings 452 of the conductor 446 are disposed between the protrusion 430 of the first lead retaining member 424 and one protrusion 432 of the second lead retaining member 426 when the first and second lead retaining members are engaged with the elongated body 444 of the lead 428 of the medical device. In one or more embodiments, the second lead retaining member 426 of the cover 414 includes a second protrusion 433 laterally spaced from the protrusion 432 of the second lead retaining member such that the protrusion 430 of the first lead retaining member 424 of the base 402 is laterally disposed between the protrusion 432 and the second protrusion 433 of the second lead retaining member when the cover is connected to the base as is shown in FIG. 11.

Any suitable technique or techniques can be utilized to dispose an apparatus (e.g., anchoring apparatus 400 of FIGS. 1-12) on a cranium of a patient. For example, FIGS. 14-22 are various views of one embodiment of a placement tool 600 for an apparatus 602 to be fastened to a cranium (e.g., cranium 13 of FIGS. 1A-B) with a fastener 604 around a burr hole (e.g., burr hole 11 of FIG. 1B) formed through the cranium. The apparatus 602 can include any suitable apparatus, e.g., apparatus 400 of FIGS. 1-12. All of the design considerations and possibilities regarding the apparatus 400 of FIGS. 1-12 apply equally to the apparatus 602 of FIGS. 16-22.

The placement tool 600 includes a receptacle 606 adapted to hold the fastener 604, where the receptacle includes a channel 608 extending between an upper opening 610 of the receptacle and a lower opening 612 of the receptacle along a channel axis 614. The placement tool 600 further includes a retainer 616 disposed within the channel 608 of the receptacle 606. The retainer 616 includes a recess or a protrusion 618 adapted to restrain the fastener 604 against movement. Further, the fastener opening 622 of the apparatus 602 is configured to align with the channel axis 614 of the channel 608 of the receptacle 606 when the placement tool is engaged with the apparatus. The tool 600 can also include an optional arm 620 that extends laterally from the receptacle 606, where the arm is configured to align the fastener opening 622 of the apparatus 602 with the channel axis 614 of the channel 608 of the receptacle 606 when the placement tool is engaged with the apparatus. In one or more embodiments, the receptacle 606 can extend from the central portion 624 without being coupled or connected via arms to the central portion.

The placement tool 600 can have any suitable dimensions and take any suitable shape or shapes. In one or more embodiments, the tool 600 includes a central portion 624 that is generally aligned along a central axis 626 of the tool. As used herein, the term "generally aligned" means that the central portion 624 is substantially rotationally symmetrical about the central axis 626 of the tool 600. The channel axis 614 of the channel 608 of the receptacle 606 extends at an angle 628 (FIG. 15) with the central axis of the tool. The angle 628 can include any suitable angle greater than 0 degrees and less than 90 degrees to conform to the curvature of the cranium. In other embodiments, the angle 628 could be, e.g., 0 degrees, at least 5 degrees, at least 10 degrees, at least 15 degrees, or at least 20 degrees. In other embodiments, the angle 628 can be no greater than 45 degrees, 40 degrees, 35 degrees, 30 degrees, or 25 degrees. In yet other embodiments, the angle 628 may be greater than 45 degrees but less than 90 degrees.

The central portion 624 of the tool 600 can be configured to engage with an upper surface 630 of the apparatus 602 as is illustrated in FIGS. 16-21. For example, the central portion 624 can include a lower part 632 that is adapted to extend through an orifice 634 of the apparatus 602 and to fit within the burr hole. For example, opposing elastically flexible legs 636 of the central portion 624 can be pushed toward one another to insert the lower part 632 of the central portion through the orifice 634 of the apparatus 602, and then can be released so that tool 600 holds the apparatus in a press fit. The lower part 632 can be configured to fit within the cranial burr hole so that the tool 600 serves to center orifice 634 of the apparatus 602 over burr hole, for example, as illustrated in FIGS. 1B-C. In one or more embodiments, the tool 600 does not include the central portion 624.

The receptacle 606 can take any suitable shape or shapes and have any suitable dimensions. Further, the channel 608 can also take any suitable shape or shapes and have suitable dimensions. The channel 608 includes an inner wall 638. In one or more embodiments, the channel 608 can have any suitable cross-sectional shape formed by the inner wall 638 in a plane substantially orthogonal to the channel axis 614. In one or more embodiments, this cross-sectional area can take an elliptical (e.g., circular) shape. Further, the receptacle 606 can have any suitable length as measured between the upper opening 610 and a lower opening 612. In one or more embodiments, the length of the receptacle 606 is at least two times the length of the fastener 604. In one or more embodiments, the length of the receptacle 606 is at least three times the length of the fastener 604.

In one or more embodiments, the receptacle 606 can include an extension 642 that defines a lower opening 612 of the receptacle. The extension 642 can be adapted to shroud the fastener opening 622 of the apparatus 602 when the tool 600 is engaged with the apparatus. The extension 642 can take any suitable shape or shapes and have any suitable dimensions.

Disposed within the channel 608 is the retainer 616. The retainer 616 can be disposed in any suitable location within the channel 608. The retainer 616 can include any suitable element or component that is adapted to restrain the fastener 604 against movement. For example, the retainer 616 can be adapted to prevent the fastener 604 from being displaced from the receptacle 606 in a direction from the lower opening 612 to the upper opening 610 of the receptacle. In one or more embodiments, the retainer 616 includes the recess or protrusion 618 that is adapted to restrain the fastener 604 against movement. In one or more embodiments, the retainer 616 can include one or more recesses and one or more protrusions.

Figure 18:
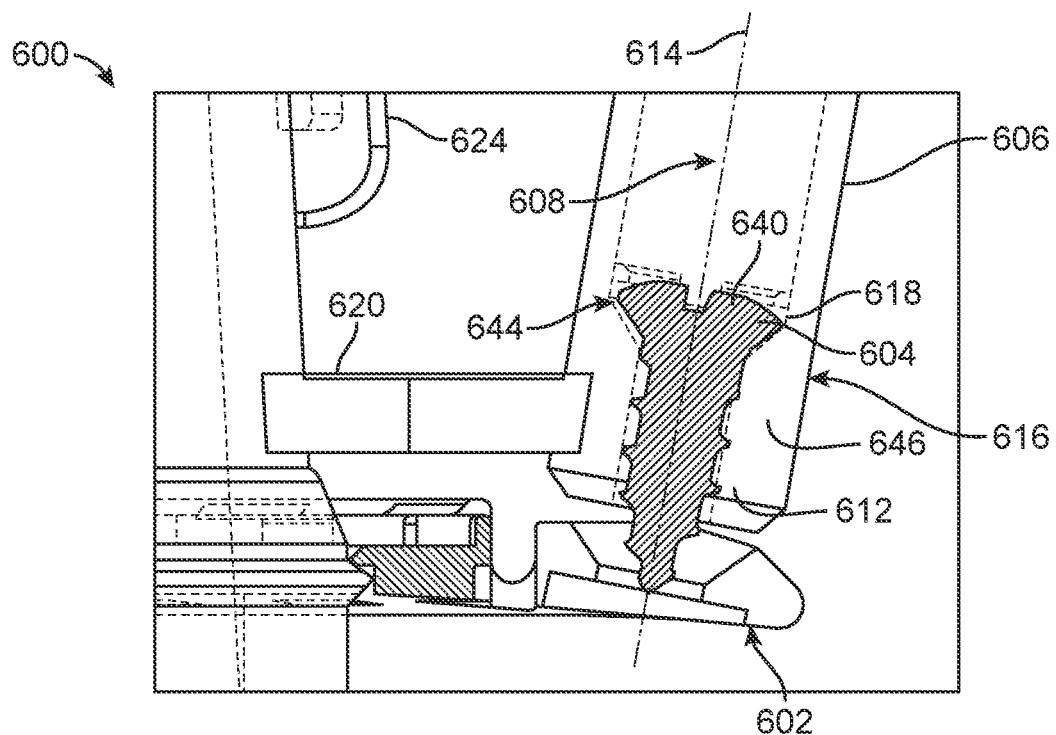
FIG. 18 is a schematic cross-section view of portions of the tool and apparatus of FIG. 16.
Figure 19:
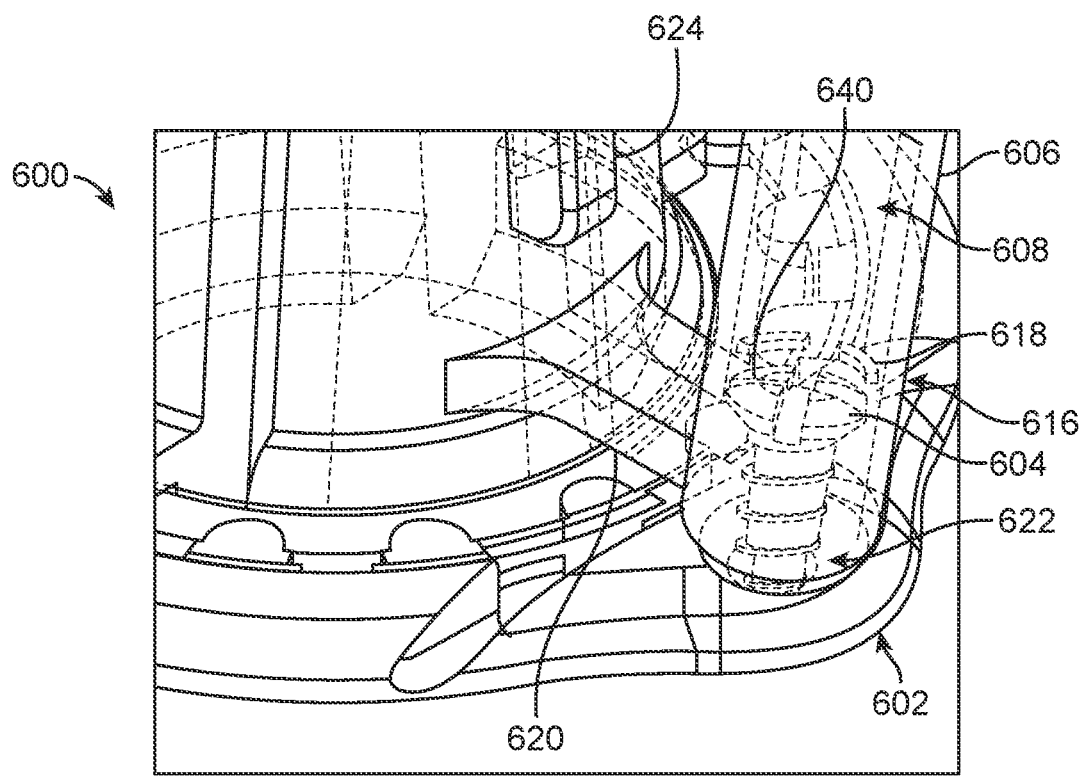
FIG. 19 is a schematic perspective view of the portions of the tool and apparatus of FIG. 18.

As shown in the illustrated embodiment, the retainer 616 includes protrusions 618. The retainer 616 can include any suitable number of protrusions 618. Further, such protrusion 618 can take any suitable shape or shapes and have any suitable dimensions. In one or more embodiments, the protrusions 618 are adapted to engage the fastener 604. For example, the protrusions 618 can be adapted to engage a head 640 of the fastener 604 as shown in FIGS. 18-19. In one or more embodiments, the retainer 616 can include a recess 644 as shown in FIG. 18. A portion of the fastener 604 can be adapted to be disposed within the recess 644. The recess 644 can be disposed in any suitable location relative to the channel 608. In one or more embodiments, the recess 644 is formed between protrusions 618 and the lower opening 612 of the channel 608. The recess 644 can take any suitable shape or shapes. As shown in FIG. 18, the recess 644 takes a shape that is similar to a shape of the head 640 of the fastener 604.

The retainer 616 can be formed separately from the receptacle 606 and disposed within the channel 608 of the receptacle using any suitable technique or techniques. In one or more embodiments, the retainer 616 can be integral with the receptacle, i.e., the retainer is unitarily formed of a single material with the receptacle 606. For example, in one or more embodiments, the protrusions 618 are formed or disposed on the inner wall 638 of the channel 608.

The retainer 616 can also include a receiver 646 as shown in FIG. 18. The receiver 646 can take any suitable shape or shapes and have any suitable dimensions. In one or more embodiments, the receiver 646 is disposed between the recess or protrusions 618 and the lower opening 612 of the receptacle 606. The receiver 646 is adapted to engage the fastener 604 to provide a friction fit for the fastener as can be seen in FIG. 18. The receiver 646 can include a cross-sectional area in a plane substantially orthogonal to the channel axis 614 of the receptacle 606 that is less than a cross-sectional area of the channel 608 in the plane substantially orthogonal to the channel axis.

In general, the receptacle 606 can be adapted to expand outwardly from the channel axis 614 such that the fastener 604 can be directed through the lower opening 612 of the receptacle 606. In one or more embodiments, the receiver 646 of the retainer 616 can be adapted to deform such that the fastener 604 can be directed through the lower opening 612 of the receptacle 606. Such deformation can be provided by the structure of the receiver 646 and/or the material utilized to form the receiver.

The tool 600 also includes the optional arm 620 that extends laterally from the receptacle 606. In one or more embodiments, the arm 620 extends substantially orthogonally to the central axis 626. The arm 620 can be adapted to align the fastener opening 622 (FIG. 19) of the apparatus 602 with the channel axis 614 of the channel 608 of the receptacle 606 when the placement tool 600 is engaged with the apparatus 602. The arm 620 can take any suitable shape or shapes and have any suitable dimensions. In one or more embodiments, the arm 620 is connected to the central portion 624 of the tool 600. Further, the arm 620 can be connected to the central portion 624 and the retainer 616 using any suitable technique or techniques. In one or more embodiments, the arm 620 is integral with at least one of the central portion 624 or the receptacle 606.

The tool 600 can include any suitable number of receptacles 606. For example, the tool 600 includes a second receptacle 648 adapted to hold a second fastener 650. In embodiments where the tool 600 includes the second receptacle 648, the receptacle 606 can be referred to as the first receptacle, the channel 608 as the first channel, the channel axis 614 as the first channel axis, the retainer 616 as the first retainer, the fastener 604 as the first fastener, the fastener opening 622 of the apparatus 602 as the first fastener opening, and the arm 620 as the first arm. The second receptacle 648 can include any suitable receptacle, e.g., receptacle 606. All of the design considerations and possibilities regarding the receptacle 606 apply equally to the second receptacle 648. The second receptacle 648 includes a second channel 652 that extends between an upper opening 654 and a lower opening 656 along a second channel axis 658. The tool 600 can also include a second retainer 660 disposed within the second channel 652 of the second receptacle 648. The second retainer 660 includes a recess or protrusion 662 adapted to engage the second fastener 650. Further, the second retainer 660 can include a receiver 664 disposed between the recess or protrusion 662 and the lower opening 656 of the channel 652 of the second receptacle 648. The second receiver 664 is adapted to engage the second fastener 650 to provide a friction fit for the second fastener.

The tool 600 can also include a second arm 666 extending laterally from the second receptacle 648. The second arm 666 is adapted to align a second fastener opening 668 (FIG. 16) of the apparatus 602 with the second channel axis 658 when the tool is engaged with the apparatus. The second arm 666 can position the second receptacle 648 such that the second channel axis 658 forms an angle 670 with the central axis 626. The angle 670 can be any suitable angle, e.g., the same angles described herein regarding angle 628.

Figure 20:
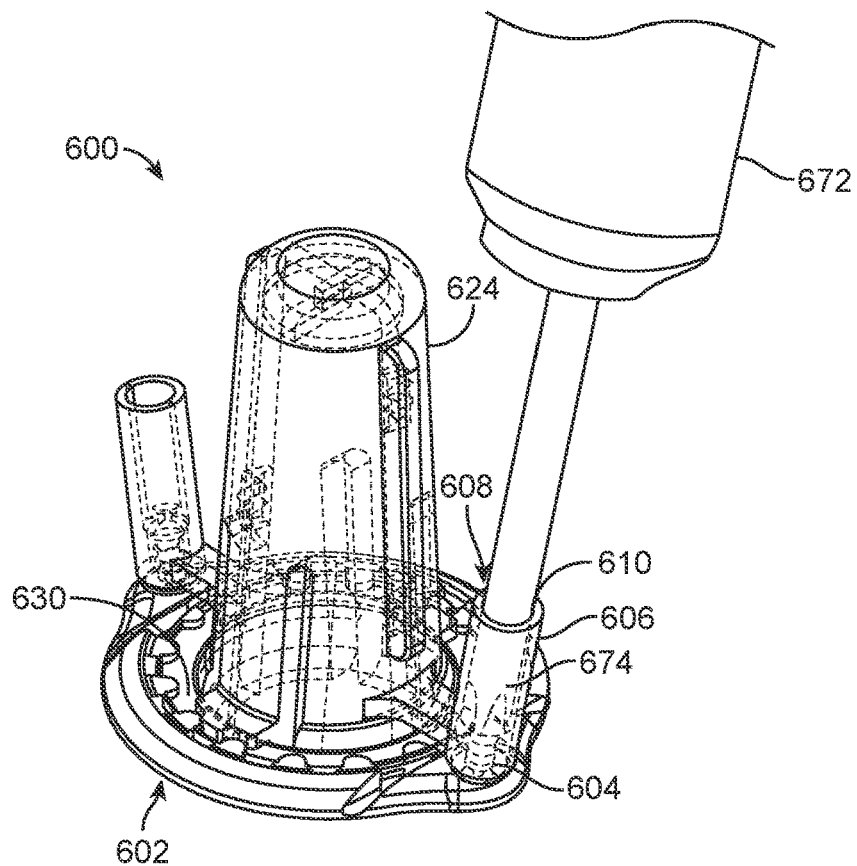
FIG. 20 is a schematic perspective view of the placement tool and apparatus of FIG. 16 with a driving tool inserted into a receptacle of the placement tool.

As described herein, the first and second receptacles 606, 648 can include any suitable first and second channels 608, 652 respectively. In one or more embodiments, at least one of the first and second channels 608, 652 can be adapted to align at least one of the fasteners 604, 650 with a portion of a driving tool 672 when the tool is disposed within the channel. For example, as shown in FIG. 20, the channel 608 of the first receptacle 606 is adapted to align the fastener 604 with a portion of the driving tool 672 when the driving tool is disposed within the channel. Any suitable technique or techniques can be utilized to align the driving tool 672 with the fastener 604. In one or more embodiments, the inner surface 638 of the channel 608 can have a circumference in a plane perpendicular to the channel axis 614 that is substantially equal to a circumference of an outer surface 674 of the portion of the driving tool 672 that is inserted into the channel.

Figure 21:
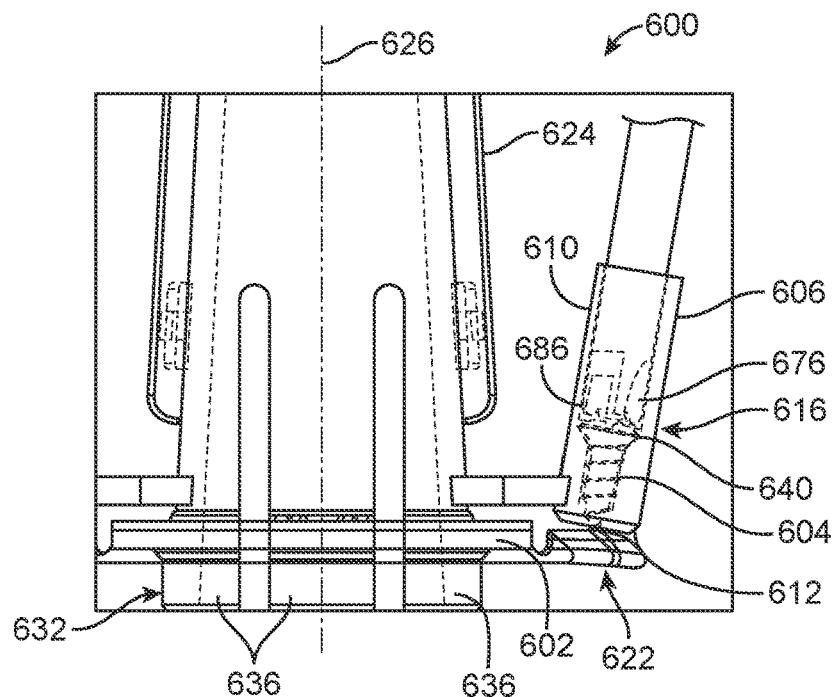
FIG. 21 is a schematic side view of the placement tool and apparatus of FIG. 16 with the driving tool inserted into the receptacle of the placement tool and engaged with a fastener.
Figure 22:
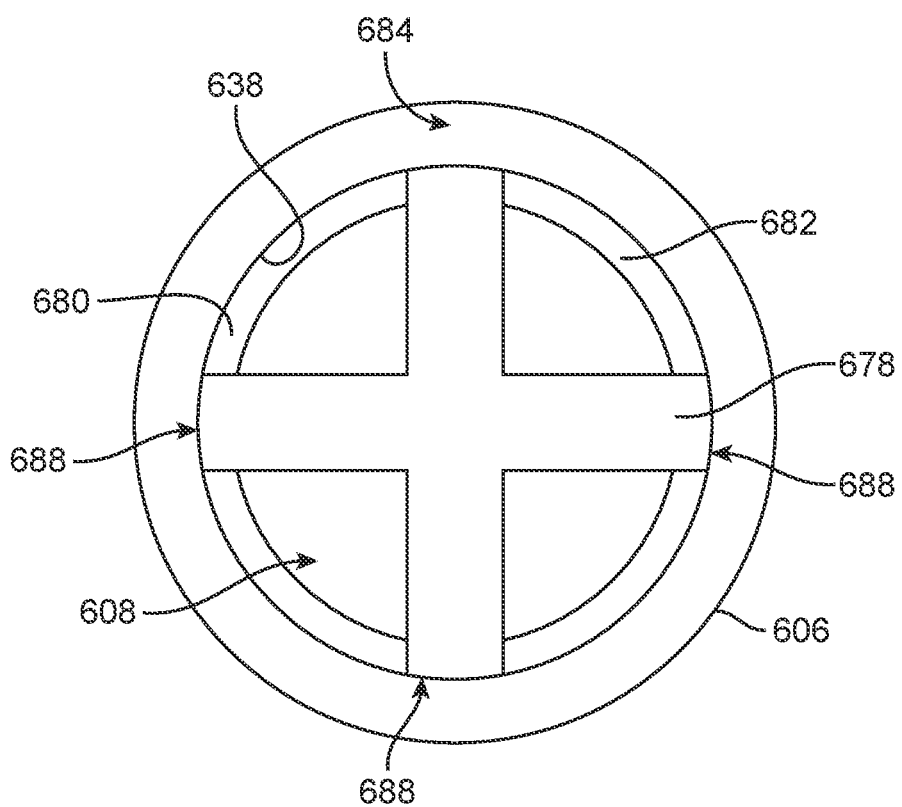
FIG. 22 is a schematic top view of the receptacle of the placement tool of FIG. 16.

Further, the retainer 616 of the first receptacle 606 and/or the retainer 660 of the second receptacle 648 can be adapted to guide a blade 676 of the driving tool 672 into a groove 678 in the head 640 of the fastener 604 (FIG. 22). For example, the 616 of the first receptacle 606 can include first and second protrusions 680, 682 that extend from the inner surface 638 of the channel 608 of the receptacle as shown in FIG. 22. The first and second protrusions 680, 682 are separated by a slot 684 that is substantially parallel to the channel axis 614. The slot 684 is adapted to receive the blade 676 disposed on an end 686 of the driving tool 672 and guide the blade into the groove 678 of the head 640 of the fastener 604 as shown in FIGS. 21-22. In one or more embodiments, protrusions 618 of retainer 16 can form additional slots 688 such that the retainer can accommodate a Phillips-type driving tool 672.

In one or more embodiments, the protrusion 618 can be disposed on the inner surface 638 of the channel 608 and can continuously extend around the circumference of the inner surface of the channel, where the protrusion includes a slot 688 that is substantially parallel to the channel axis 614. This slot is adapted to receive the blade 676 disposed on the end 686 of the driving pool 672 and direct the blade into the groove 678 in the head 640 of the fastener 604. In one or more embodiments, an additional slot 688 can be formed such that the retainer 616 can accommodate a flathead-type driving tool 672.

What is claimed is:

1. A placement tool for an apparatus to be fastened to a cranium with a fastener around a burr hole formed through the cranium, the placement tool comprising:
   a receptacle adapted to hold the fastener, wherein the receptacle comprises a channel extending between an upper opening of the receptacle and a lower opening of the receptacle along a channel axis;
   a central portion generally aligned along a central axis of the tool, wherein the channel axis of the channel of the receptacle extends at an angle with the central axis of the tool; and
   a retainer disposed within the channel of the receptacle, the retainer comprising a recess or a protrusion adapted to restrain the fastener against movement, wherein the retainer is adapted to prevent the fastener from being displaced from the receptacle in a direction from the lower opening to the upper opening of the receptacle;
   wherein a fastener opening of the apparatus is configured to align with the channel axis of the channel of the receptacle when the placement tool is engaged with the apparatus.

2. The tool of claim 1, wherein the central portion is configured to engage with an upper surface of the apparatus.

3. The tool of claim 1, wherein a lower part of the central portion is adapted to extend through an orifice of the apparatus and to fit within the burr hole.

4. The tool of claim 1, wherein the receptacle further comprises an extension defining the lower opening of the receptacle, the extension being adapted to shroud the fastener opening of the apparatus when the tool is engaged with the apparatus.

5. The tool of claim 1, wherein the retainer comprises a recess, and wherein a portion of the fastener is adapted to be disposed within the recess.

6. The tool of claim 1, wherein the retainer comprises a protrusion adapted to engage the fastener.

7. The tool of claim 1, wherein the retainer is unitarily formed of a single material with the receptacle.

8. The tool of claim 1, wherein the recess or protrusion of the retainer is disposed on an inner wall of the channel of the receptacle.

9. The tool of claim 1, wherein the retainer further comprises a receiver disposed between the recess or protrusion and the lower opening of the channel, wherein the receiver is adapted to engage the fastener to provide a friction-fit for the fastener.

10. The tool of claim 9, wherein the receiver comprises a cross-sectional area in a plane substantially orthogonal to the channel axis of the receptacle that is less than a cross-sectional area of the channel in the plane substantially orthogonal to the channel axis.

11. The tool of claim 9, wherein the receiver of the retainer is adapted to deform such that the fastener can be directed through the lower opening of the receptacle.

12. The tool of claim 1, further comprising an arm that extends laterally from the receptacle, wherein the arm is configured to align the fastener opening of the apparatus with the channel axis of the channel of the receptacle when the placement tool is engaged with the apparatus.

13. The tool of claim 12, wherein the arm extends substantially orthogonally to a central axis along which a central portion of the placement tool is aligned.

14. The tool of claim 12, wherein the receptacle is a first receptacle, the channel is a first channel, the channel axis is a first channel axis, the fastener is a first fastener, the fastener opening is a first fastener opening and the arm is a first arm, the tool further comprising:
   a second receptacle adapted to hold a second fastener, wherein the second receptacle comprises a second channel that extends between an upper opening and a lower opening of the second receptacle along a second channel axis; and
   a second arm extending laterally from the second receptacle, wherein the second arm is adapted to align a second fastener opening of the apparatus with the second channel axis when the tool is engaged with the apparatus.

15. The tool of claim 14, wherein the retainer is a first retainer, the tool further comprising a second retainer disposed within the second channel of the second receptacle, wherein the second retainer comprises a recess or a protrusion adapted to engage the second fastener.

16. The tool of claim 15, wherein the retainer further comprises a first receiver disposed between the recess or protrusion and the lower opening of the channel, wherein the first receiver is adapted to engage the fastener to provide a friction-fit for the fastener, wherein the second retainer further comprises a second receiver disposed between the recess or protrusion and the lower opening of the channel of the second receptacle, wherein the second receiver is adapted to engage the second fastener to provide a friction-fit for the second fastener.

17. The tool of claim 1, wherein the channel axis of the receptacle is configured to be positioned perpendicular to the cranium.

18. The tool of claim 1, wherein the retainer comprises a recess and a protrusion each adapted to restrain the fastener against movement.

19. A placement tool for an apparatus to be fastened to a cranium with a fastener around a burr hole formed through the cranium, the placement tool comprising:
   a receptacle adapted to hold the fastener, wherein the receptacle comprises a channel extending between an upper opening of the receptacle and a lower opening of the receptacle along a channel axis;
   a retainer disposed within the channel of the receptacle, the retainer comprising a recess or a protrusion adapted to restrain the fastener against movement, wherein the retainer is adapted to prevent the fastener from being displaced from the receptacle in a direction from the lower opening to the upper opening of the receptacle;
   an arm extending laterally from the receptacle, wherein the arm is adapted to align a fastener opening of the apparatus with the channel axis of the channel of the receptacle when the placement tool is engaged with the apparatus; and
   a central portion generally aligned along a central axis of the tool, wherein the channel axis of the channel of the receptacle extends at an angle with the central axis of the tool;
   wherein the channel is adapted to align the fastener with a portion of a driving tool when disposed within the channel.

20. The tool of claim 19, wherein an inner surface of the channel has a circumference in a plane perpendicular to the channel axis that is substantially equal to a circumference of an outer surface of the portion of the driving tool.

21. The tool of claim 19, wherein a length of the receptacle is at least two times a length of the fastener.

22. The tool of claim 21, wherein the length of the receptacle is at least three times a length of the fastener.

23. The tool of claim 19, wherein the retainer comprises first and second protrusions extending from an inner surface of the channel of the receptacle, wherein the first and second protrusions are spaced apart by a slot that is substantially parallel to the channel axis, wherein the slot is adapted to receive a blade disposed on an end of the driving tool and guide the blade into a groove in the of the fastener.

24. The tool of claim 19, wherein the retainer comprises a protrusion that is disposed on an inner surface of the channel and continuously extends around a circumference of the inner surface of the channel, wherein the protrusion comprises a slot that is substantially parallel to the channel axis, wherein the slot is adapted to receive a blade disposed on an end of the driving tool and guide the blade into a groove in the head of the fastener.

25. The tool of claim 19, wherein the retainer comprises a recess and a protrusion each adapted to restrain the fastener against movement.

* * * * *